(12) United States Patent
Theis et al.

(10) Patent No.: US 8,862,370 B2
(45) Date of Patent: Oct. 14, 2014

(54) NOX CONTROL DURING ENGINE IDLE-STOP OPERATIONS

(75) Inventors: Joseph Robert Theis, Rockwood, MI (US); James Michael Kerns, Trenton, MI (US); Michael James Uhrich, West Bloomfield, MI (US); Giovanni Cavataio, Dearborn, MI (US); Thomas G. Leone, Ypsilanti, MI (US); Jeffrey Allen Doering, Canton, MI (US); Todd Anthony Rumpsa, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 271 days.

(21) Appl. No.: 13/565,454

(22) Filed: Aug. 2, 2012

(65) Prior Publication Data

US 2014/0039781 A1    Feb. 6, 2014

(51) Int. Cl.
*F02D 41/26*      (2006.01)

(52) U.S. Cl.
USPC ..................................... 701/112; 701/113

(58) Field of Classification Search
USPC ........... 123/339.1, 339.12, 179.3, 179.4, 672, 123/680, 681, 685, 704, 443; 701/103, 109, 701/112, 113; 60/295, 303, 304, 319
See application file for complete search history.

(56) References Cited

U.S. PATENT DOCUMENTS

| | | | |
|---|---|---|---|
| 6,823,663 B2 * | 11/2004 | Hammerle et al. | 60/286 |
| 6,969,492 B1 | 11/2005 | Goerigk et al. | |
| 7,059,114 B2 | 6/2006 | Tang et al. | |
| 7,093,427 B2 * | 8/2006 | van Nieuwstadt et al. | 60/286 |
| 7,892,508 B2 | 2/2011 | Katoh | |
| 8,041,498 B2 | 10/2011 | Brown et al. | |
| 8,516,808 B2 * | 8/2013 | Aoyama et al. | 60/301 |
| 2007/0028601 A1 | 2/2007 | Duvinage et al. | |
| 2010/0037597 A1 * | 2/2010 | Eckhoff et al. | 60/286 |
| 2010/0058746 A1 | 3/2010 | Pfeifer et al. | |
| 2011/0252766 A1 | 10/2011 | Ramanathan et al. | |

FOREIGN PATENT DOCUMENTS

WO      2009080152 A1      7/2009

OTHER PUBLICATIONS

Leone, Thomas G. et al., "Engine Control for Catalyst Regenerations," U.S. Appl. No. 13/868,742, filed Apr. 23, 2013, 49 pages.
Kerns, James Michael et al., "NOX Control During Cylinder Deactivation,"U.S. Appl. No. 13/565,490, filed Aug. 2, 2012, 62 pages.

* cited by examiner

*Primary Examiner* — Hai Huynh
(74) *Attorney, Agent, or Firm* — Julia Voutyras; Alleman Hall McCoy Russell & Tuttle LLP

(57) ABSTRACT

Methods and systems are provided for improving engine exhaust emissions while enabling exhaust catalyst regeneration following an engine lean event. Prior to a VDE event, or prior to an engine idle-stop, ammonia is produced and stored on an exhaust underbody SCR catalyst. Then, during the engine restart after the VDE mode or the idle-stop, the stored ammonia is used to treat exhaust NOx species while an upstream exhaust underbody three-way catalyst is regenerated.

20 Claims, 10 Drawing Sheets

NOX CONTROL DURING ENGINE IDLE-STOP OPERATIONS

TECHNICAL FIELD

This application relates to adjusting exhaust catalyst regeneration following a lean event such as an engine idle-stop to achieve exhaust NOx control.

BACKGROUND AND SUMMARY

Engine emission control systems may include one or more exhaust catalysts to address the various exhaust components. These may include, for example, three-way catalysts, NOx storage catalysts, light-off catalysts, SCR catalysts, etc. Engine exhaust catalysts may require periodic regeneration to restore catalytic activity and reduce catalyst oxidation. For example, catalysts may be regenerated by injecting sufficient fuel to produce a rich environment and reduce the amount of oxygen stored at the catalyst. As such, fuel consumed during catalyst regeneration can degrade engine fuel economy. Accordingly, various catalyst regeneration strategies have been developed.

One example approach is shown by Georigk et al. in U.S. Pat. No. 6,969,492. Therein, an emission control device includes catalytic converter stages generated by at least two catalysts arranged in series. Specifically, the catalytic stages include a three-way catalyst arranged in series with (e.g., upstream of) a NOx reduction catalyst. The different ammonia storage performance of the different catalysts enables NOx reduction to be improved and reduces the need for catalyst regeneration. Another example approach is shown by Eckhoff et al. in WO 2009/080152. Therein, an engine exhaust system includes multiple NOx storage catalysts with an intermediate SCR catalyst, and an exhaust air-to-fuel ratio is continually alternated between rich and lean phases based on differences between an air-to-fuel ratio upstream of a first NOx storage catalyst and an air-to-fuel ratio downstream of a second NOx storage catalyst.

However, the inventors herein have identified potential issues with such approaches. Catalyst regeneration strategies are not only dependent on the specific configuration and nature of the different exhaust catalysts in the emission control device, but for engine systems wherein the engine can be selectively deactivated responsive to idle-stop conditions, the regeneration is also affected by the idle-stop operations performed during a vehicle drive cycle. This includes, for example, a number, frequency, and duration of the idle-stop operations performed during the vehicle's drive cycle. In particular, during an idle-stop when the engine is deactivated and fuel is shut off for the shut-down, the engine still spins a few more times. This spinning pumps air over an exhaust three-way catalyst, causing the catalyst to become oxidized and degrading its ability to reduce NOx when the engine is reactivated. Likewise, before the engine is restarted from idle-stop, the engine is spun a few times, providing another opportunity during which air can be pumped over the exhaust catalyst. While enrichment can be used to quickly regenerate the three-way catalyst upon engine reactivation, the enrichment leads to a fuel penalty. In addition, delays in engine restart can degrade engine performance.

In one example, some of the above issues may be at least partly addressed by a method for an engine comprising, during engine running, flowing exhaust gas through a first, upstream catalyst and then a second, downstream catalyst to store at least some exhaust ammonia on the first catalyst. The method further comprises selectively deactivating the engine in response to an idle-stop and during an engine restart from the idle-stop, adjusting regeneration of a third catalyst upstream of the first catalyst based on an ammonia content of the first catalyst. In addition, during high engine loads, regeneration of the second catalyst can also be adjusted based on the ammonia content of the first catalyst. In this way, ammonia generated during stoichiometric engine operation can be stored on the first exhaust catalyst and advantageously used to reduce exhaust NOx species during an engine restart from idle-stop conditions while the second and third exhaust catalysts are regenerated.

In one example, an idle-stop engine may be configured with a common exhaust manifold underbody. The underbody may include a first, SCR exhaust catalyst coupled upstream of, and in face-to-face brick contact with a second, three-way exhaust catalyst. As such, each of the first and second exhaust catalysts may be downstream of a third close-coupled three-way exhaust catalyst. During engine operation, ammonia generated by the third exhaust catalyst can be stored in the first, SCR catalyst, and retained thereon while the engine is deactivated responsive to idle-stop conditions. An air-to-fuel ratio during an engine operation prior to the idle-stop may be adjusted to be stoichiometric, or richer than stoichiometry, to store a desired amount of ammonia at the first catalyst by the time an idle-stop is performed and the engine is shut down. By storing the generated ammonia on the first, SCR catalyst, ammonia storage on the second three-way catalyst is reduced, thereby also lowering unwanted oxidation of ammonia to NOx at the second catalyst during the idle-stop. During a subsequent engine restart, the ammonia retained on the first, SCR catalyst may be used to reduce NOx species, while an air-to-fuel ratio is adjusted based on the ammonia content remaining on the first, SCR catalyst.

The ammonia content may have changed during the idle-stop. In particular, the ammonia content may have changed based on a duration of the idle-stop as well a degree of catalyst cooling or heating incurred during the idle-stop. As such, cooling of the first SCR catalyst may increase the catalyst's ammonia storage capacity until a threshold temperature is reached, allowing it to store more ammonia. However, as the temperature of the first catalyst cools below the threshold temperature, the ammonia storage capacity of the catalyst may start to fall. Thus, if ammonia was stored on the first catalyst, as the temperature of the first catalyst falls below the threshold temperature during the idle-stop, some of the stored ammonia may be released, changing the ammonia content of the first catalyst by the time an engine restart from idle-stop is requested. Additionally, when exhaust is flowing through the emission control device, it carries heat away from the catalysts, allowing the ammonia storage capacity of the SCR catalyst to be increased. Then, when the engine is stopped during the idle-stop, the SCR catalyst temperature may temporarily increase, causing the SCR catalyst to oxidize some of the stored ammonia to nitrogen or NO using the oxygen pumped in the 2-3 engine revolutions after fuel shut-off. However, if the idle-stop is for a longer duration, the catalyst may substantially cool below the threshold temperature, causing some of the stored ammonia to be lost. In the same way, over a given vehicle drive cycle (e.g., between a time at which the vehicle operator keys on the vehicle to a time at which the operator keys off the vehicle), the engine may be idle-stopped multiple times, and the air-to-fuel ratio at an engine restart may be adjusted based on how often the engine is idle-stopped.

In this way, an air-to-fuel ratio may be adjusted while an engine is operating to charge an underbody exhaust SCR catalyst with ammonia and protect an underbody three-way catalyst from being charged with the ammonia. By using the stored ammonia during a subsequent engine restart from idle-stop, an amount of fuel required to regenerate the close-coupled and underbody three-way catalysts can be reduced, providing fuel economy benefits.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to a method for adjusting an exhaust air-to-fuel ratio of an engine so as to reduce an exhaust catalyst regeneration requirement following a lean engine operation. The lean operation may include an idle-stop operation, such as in the engine system of FIGS. 1 and 3, or cylinder deactivation in a variable displacement engine, such as in the engine system of FIGS. 2A-B and 3. Still other lean operations may include a deceleration fuel shut-off operation (DFSO). An engine controller may be configured to perform a control routine, such as the example routines of FIGS. 4A-B, to flow stoichiometric or rich exhaust gas over a first exhaust catalyst and charge the catalyst with ammonia. During a subsequent engine restart from idle-stop, the stored ammonia can be used to reduce NOx while a third close-coupled catalyst upstream of the first catalyst is regenerated and possibly a second catalyst downstream of the first catalyst is regenerated. Likewise, the controller may perform a control routine, such as the example routines of FIGS. 5A-B, to charge the first exhaust catalyst with ammonia prior to selective cylinder deactivation so that the stored ammonia can be used to reduce NOx during a subsequent cylinder reactivation from VDE mode, while the second and third catalysts are regenerated. The ammonia content on the first catalyst may be estimated (FIG. 6) based on a comparison of the ammonia produced to the ammonia consumed (or lost) during engine operation including the lean operations. Example adjustments to an exhaust air-to-fuel ratio that enable a desired amount of ammonia to be stored on the first catalyst prior to a lean engine operation are shown at FIG. 7. In this way, by pre-storing ammonia on an exhaust SCR catalyst, the regeneration requirements of an upstream close-coupled exhaust three-way catalyst can be reduced, lowering the fuel penalty incurred during regeneration without degrading the efficiency of VDE or idle-stop operations. In addition, the regeneration requirements of a downstream under-body exhaust three-way catalyst can be reduced, providing further fuel economy benefits.

Figure 1:
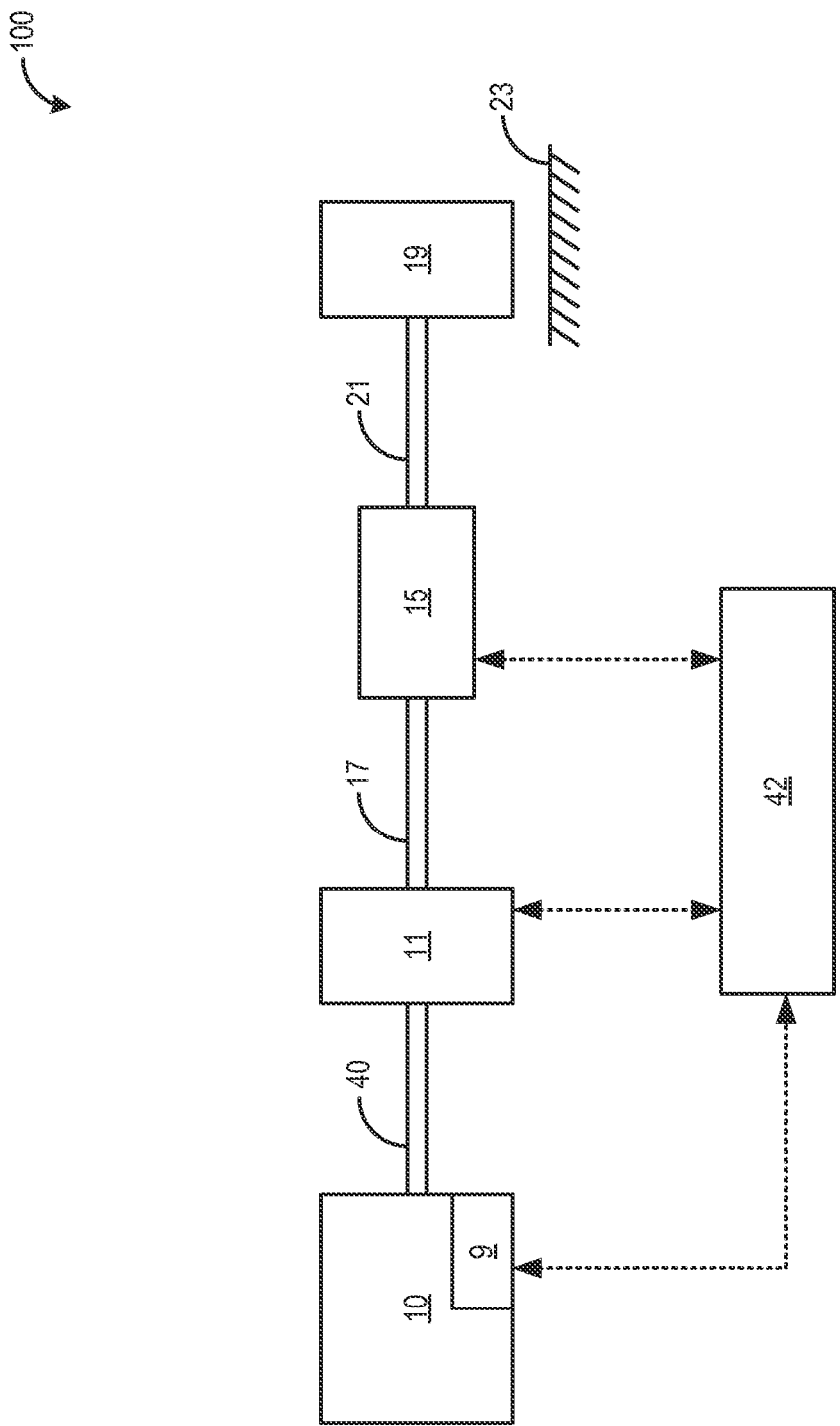
FIG. 1 shows an example vehicle drivetrain.

Referring to FIG. 1, a vehicle drivetrain 100 is shown. The drivetrain includes an internal combustion engine 10. In the depicted example, engine 10 may be selectively deactivated in response to idle-stop conditions, as further described herein with particular reference to FIGS. 2 and 4. Engine 10 is shown coupled to torque converter 11 via crankshaft 40. Engine 10 may include a starter system 9 for assisting in engine cranking at engine restarts. Torque converter 11 is also coupled to transmission 15 via turbine shaft 17. In one example, transmission 15 is a stepped-gear ratio transmission. Transmission 15 may further include various gears and transmission clutches to adjust a torque output from the transmission to wheels 19. Torque converter 11 has a bypass clutch (not shown) which can be engaged, disengaged, or partially engaged. When the clutch is either disengaged or being disengaged, the torque converter is said to be in an unlocked state. Turbine shaft 17 is also known as transmission input shaft. In one embodiment, transmission 15 comprises an electronically controlled transmission with a plurality of selectable discrete gear ratios. Transmission 15 may also comprises various other gears, such as, for example, a final drive ratio (not shown). Alternatively, transmission 15 may be a continuously variable transmission (CVT).

Transmission 15 may further be coupled to wheel 19 via axle 21. Wheel 19 interfaces the vehicle (not shown) to the road 23. Note that in one example embodiment, this powertrain is coupled in a passenger vehicle that travels on the road. While various vehicle configurations may be used, in one example, the engine is the sole motive power source, and thus the vehicle is not a hybrid-electric, hybrid-plug-in, etc. In other embodiments, the method may be incorporated into a hybrid vehicle.

An engine controller 42 may be configured to receive inputs from engine 10 and accordingly control a torque output of the engine and/or operation of torque converter 11, transmission 15, and related clutches. As one example, a torque output may be controlled by adjusting a combination of spark timing, fuel pulse width, fuel pulse timing, and/or air charge, by controlling throttle opening and/or valve timing, valve lift and boost for turbocharged engines. In the case of a diesel engine, controller 42 may also control the engine torque output by controlling a combination of fuel pulse width, fuel pulse timing, and air charge. In all cases, engine control may be performed on a cylinder-by-cylinder basis to control the engine torque output.

When idle-stop conditions are satisfied, controller 42 may selectively deactivate the engine by turning off fuel injection and spark ignition to the engine cylinders. In some embodiments, the controller may also adjust an engine throttle to bring manifold air pressures (MAP) towards barometric pressure (BP), to assist engine spin-down, while engaging the starting system 9 to the rotating engine to apply a braking torque and/or provide engine spin-down with reduced engine reversal. The engine may then be maintained in idle-stop until engine restart conditions are confirmed. As such, while the engine is spinning down to rest (un-fueled), air may be pumped through the exhaust catalysts. Likewise, during an engine restart from idle-stop, while the engine spins up, and before fueling is resumed, air may be pumped through the exhaust catalysts. This air can oxidize the catalysts, in particular, a close-coupled three-way exhaust catalyst, lowering its ability to reduce exhaust NOx species, and degrading exhaust emissions.

Figure 4A:
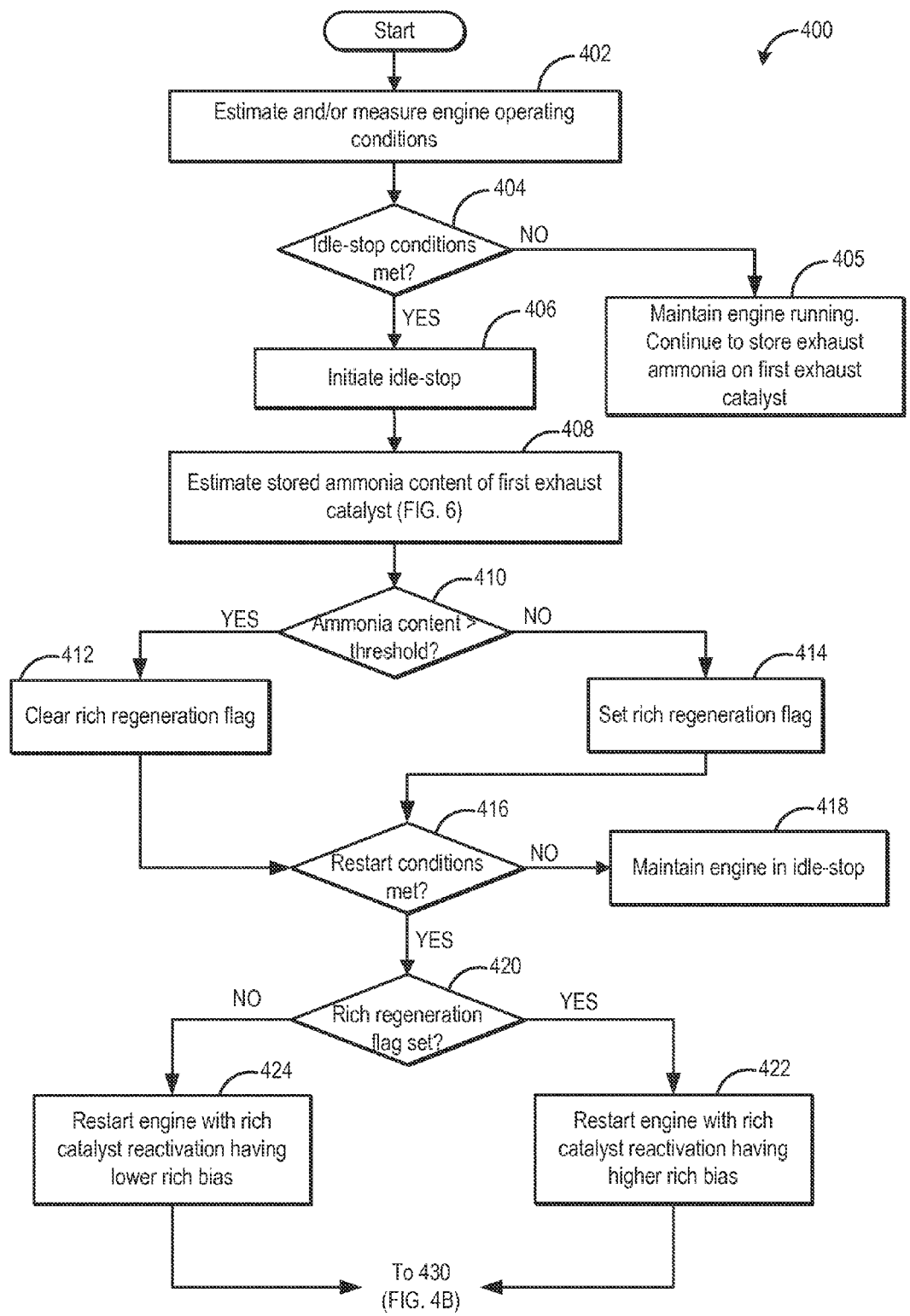
FIGS. 4A-B illustrate an example method for adjusting regeneration of a second and third exhaust catalyst during an engine restart from idle-stop based on an amount of ammonia retained on a first exhaust catalyst during the idle-stop and further based on idle stop parameters.
Figure 4B:
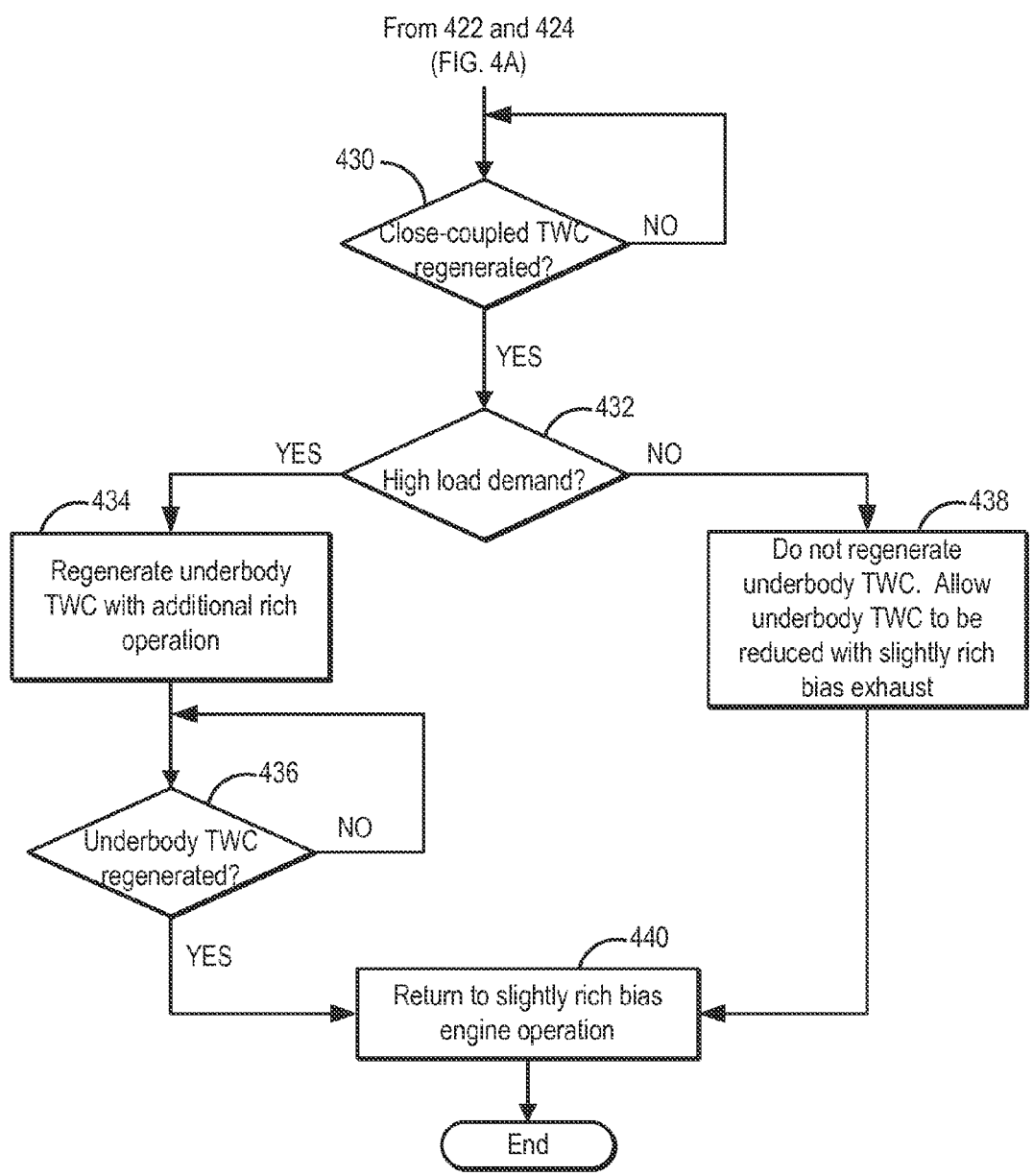

As elaborated at FIGS. 4A-B, the engine controller may also be configured with computer readable instructions for adjusting an air-to-fuel ratio during engine operation to store at least some exhaust ammonia in a first emission control device exhaust catalyst. Then, during an engine restart from idle-stop, the stored ammonia can be used to reduce exhaust NOx species while one or more other exhaust catalysts are regenerated, such as a second emission control device exhaust catalyst and a third close-coupled exhaust catalyst. The air-to-fuel ratio may be adjusted during the engine restart to adjust regeneration of at least the third close-coupled catalyst (e.g., of the second and third exhaust catalysts) based on an ammonia content stored in the exhaust catalyst at the engine restart. For example, as the ammonia content stored on the first emission control device exhaust catalyst increases, a combustion air-to-fuel ratio at engine restart from idle-stop may be increased. This reduces the fuel penalty incurred in the regeneration of the second and third exhaust catalysts. Overall fuel economy can be improved while meeting NOx emissions requirements.

Figure 2A:
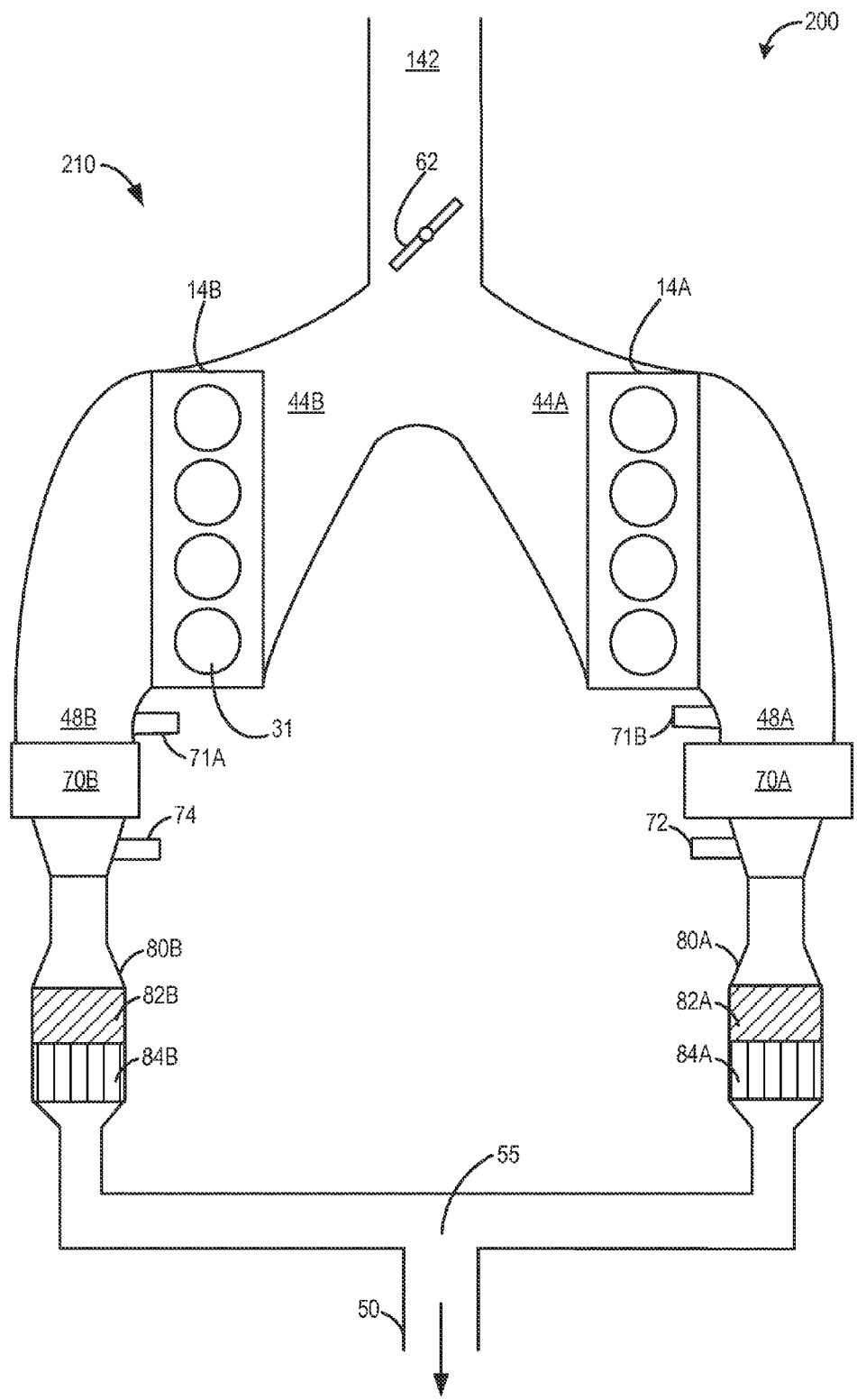
FIGS. 2A-B show example embodiments of a variable displacement engine system.
Figure 2B:
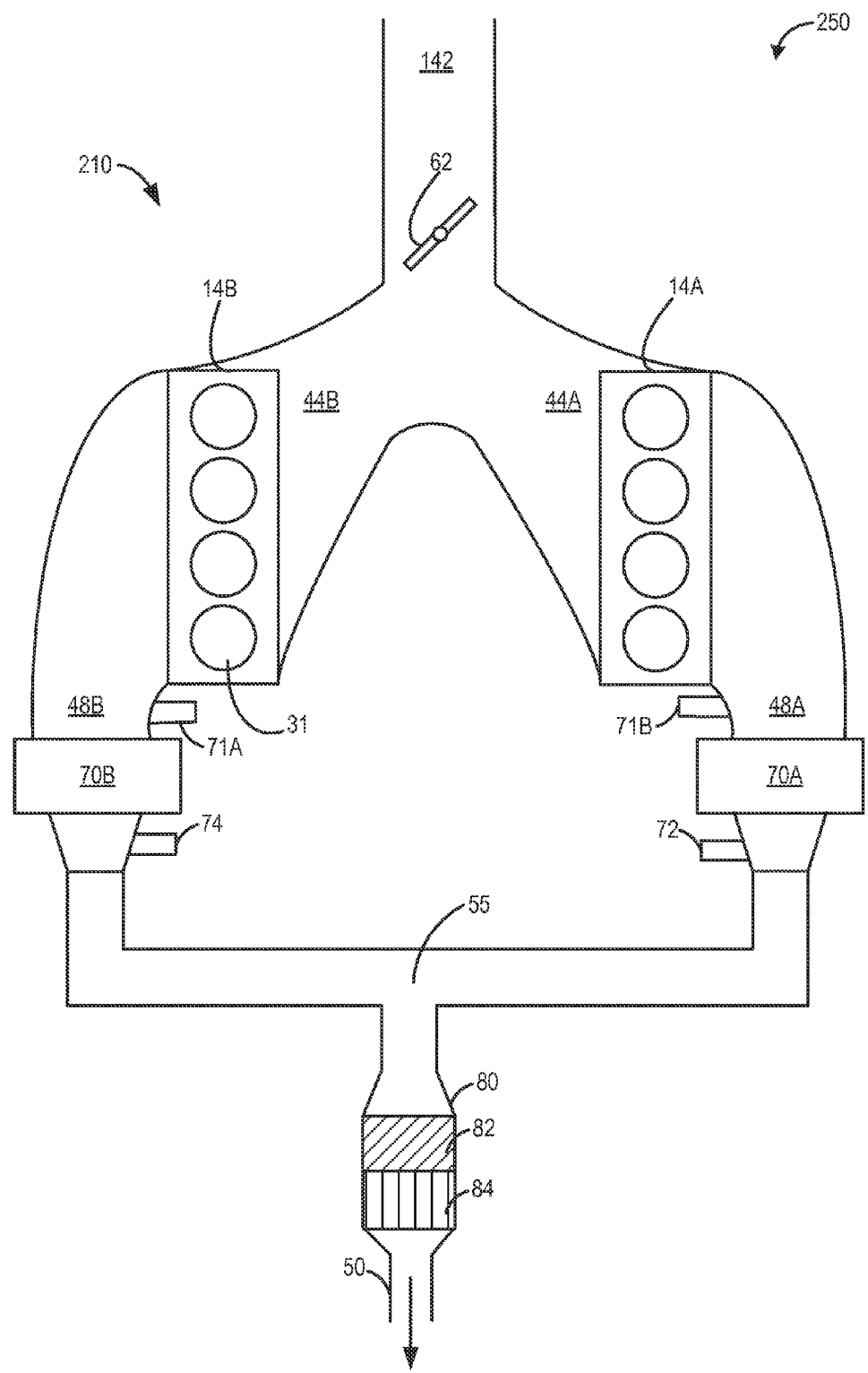

FIGS. 2A-B show example embodiments 200 and 250 of engine 210 wherein the engine is configured as a variable displacement engine (VDE). Variable displacement engine 210 includes a plurality of combustion chambers or cylinders 31. The plurality of cylinders 31 of engine 210 are arranged as groups of cylinders on distinct engine banks. In the depicted example, engine 210 includes two engine banks 14A, 14B. Thus, the cylinders are arranged as a first group of cylinders (four cylinders in the depicted example) arranged on first engine bank 14A and a second group of cylinders (four cylinders in the depicted example) arranged on second engine bank 14B. It will be appreciated that while the embodiments depicted in FIGS. 2A-B show a V-engine with cylinders arranged on different banks, this is not meant to be limiting, and in alternate embodiments, the engine may be an in-line engine with all engine cylinders on a common engine bank.

Variable displacement engine 210 can receive intake air via an intake passage 142 communicating with branched intake manifold 44A, 44B. Specifically, first engine bank 14A receives intake air from intake passage 142 via first intake manifold 44A while second engine bank 14B receives intake air from intake passage 142 via second intake manifold 44B. While engine banks 14A, 14B are shown with distinct intake manifolds, it will be appreciated that in alternate embodiments, they may share a common intake manifold or a portion of a common intake manifold. The amount of air supplied to the cylinders of the engine can be controlled by adjusting a position of throttle 62. Additionally, an amount of air supplied to each group of cylinders on the specific banks can be adjusted by varying an intake valve timing of one or more intake valves coupled to the cylinders.

With reference to FIG. 2A, combustion products generated at the cylinders of first engine bank 14A are directed to one or more exhaust catalysts in first exhaust manifold 48A where the combustion products are treated before being vented to the atmosphere. A first emission control device 70A is coupled to first exhaust manifold 48A. First emission control device 70A may include one or more exhaust catalysts, such as a close-coupled catalyst. In one example, the close-coupled catalyst at emission control device 70A may be a three-way catalyst. Exhaust gas generated at first engine bank 14A is treated at emission control device 70A before being directed to first underbody emission control device 80A. First underbody emission control device 80A may include a first underbody exhaust catalyst 82A and a second underbody exhaust catalyst 84A. In particular, the first underbody 82A and the second underbody catalyst 84A may be integrated in the underbody emission control device 80A in face-sharing contact with each other. In one example, first underbody exhaust catalyst 82A includes an SCR catalyst configured for selective catalytic reduction wherein NOx species are reduced to nitrogen using ammonia. As another example, second underbody exhaust catalyst 84A includes a three-way catalyst. First underbody exhaust catalyst 82A is positioned upstream of the second underbody exhaust catalyst 84A (in a direction of exhaust flow) in the underbody emission control device 80A but downstream of a third close-coupled exhaust catalyst (included in emission control device 70A).

Exhaust that is treated upon passage through first emission control device 70A and first underbody emission control device 80A is then directed towards exhaust junction 55 along first exhaust manifold 48A. From there, the exhaust can be directed to the atmosphere via common exhaust passage 50.

Combustion products generated at the cylinders of second engine bank 14B are exhausted to the atmosphere via second exhaust manifold 48B. A second emission control device 70B is coupled to second exhaust manifold 48B. Second emission control device 70B may include one or more exhaust catalysts, such as a close-coupled catalyst. In one example, the close-coupled catalyst at emission control device 70A may be a three-way catalyst. Exhaust gas generated at second engine bank 14B is treated at emission control device 70B before being directed to second underbody emission control device 80B. Second underbody emission control device 80B may also include a first underbody exhaust catalyst 82B and a second underbody exhaust catalyst 84B. In particular, the first underbody catalyst 82B and the second underbody catalyst 84B may be integrated in the underbody emission control device 80B in face-sharing contact with each other. In one example, first underbody exhaust catalyst 82B includes an SCR catalyst while second underbody exhaust catalyst 84B includes a three-way catalyst. Second underbody exhaust catalyst 82B is positioned upstream of the second underbody exhaust catalyst 84B (in a direction of exhaust flow) in the underbody emission control device 80B but downstream of a third close-coupled exhaust catalyst (included in emission control device 70B).

While the embodiment of FIG. 2A shows each engine bank coupled to respective underbody emission control devices, in alternate embodiments, such as shown at FIG. 2B, each engine bank is coupled to respective emission control devices 70A, 70B but to a common underbody emission control device 80. In the embodiment 250 depicted at FIG. 2B, the common underbody emission control device 80 is positioned downstream of exhaust junction 55 and common exhaust passage 55. Common underbody emission control device 80 is shown with first underbody exhaust catalyst 82 positioned upstream of and integratably coupled to second underbody exhaust catalyst 84 (in a direction of exhaust flow) in the underbody emission control device 80.

Various air-to-fuel ratio sensors may be coupled to engine 210. For example, a first air-to-fuel ratio sensor 72 may be coupled to the first exhaust manifold 48A of first engine bank 14A, downstream of first emission control device 70A while a second air-to-fuel ratio sensor 74 is coupled to the second exhaust manifold 48B of second engine bank 14B, downstream of second emission control device 70B. In further embodiments, additional air-to-fuel ratio sensors may be coupled upstream of the emission control devices, such as a first upstream air-to-fuel ratio sensor 71A coupled upstream of first emission control device 70A and a second upstream air-to-fuel ratio sensor 71B coupled upstream of second emission control device 70B. Still other air-to-fuel ratio sensors may be included, for example, coupled to the underbody emission control device(s). As elaborated at FIG. 3, the air-to-fuel ratio sensors may include oxygen sensors, such as EGO, HEGO, or UEGO sensors. In one example, the downstream air-to-fuel ratio sensors 72, 74 coupled downstream of emission control devices 70A, 70B may be HEGO sensors used for catalyst monitoring while the upstream air-to-fuel ratio sensors 71A, 71B coupled upstream of emission control devices 70A, 70B are UEGO sensors used for engine control.

One or more engine cylinders may be selectively deactivated during selected engine operating conditions. For example, during low engine loads, one or more cylinders of a selected engine bank may be selectively deactivated. This may include deactivating fuel and spark on the selected engine bank. In addition, an intake and/or exhaust valve timing may be adjusted so that substantially no air is pumped through the inactive engine bank while air continues to flow through the active engine bank. In some embodiments, the deactivated cylinders may have cylinder valves held closed during one or more engine cycles, wherein the cylinder valves are deactivated via hydraulically actuated lifters, or via a cam profile switching (CPS) mechanism in which a cam lobe with no lift is used for deactivated valves. In one example, an engine controller may selectively deactivate all the cylinders of a given engine bank (either 14A or 14B) during shift to a VDE mode and then reactivate the cylinders during a shift back to a non-VDE mode.

By selectively deactivating engine cylinders during low engine load conditions, engine pumping losses and friction losses are reduced, and fuel economy is improved. However, unique emissions challenges are presented. For example, during non-VDE or stoichiometric engine operation, ammonia is generated by the close-coupled three-way catalyst under the slightly rich conditions typically used for closed-loop control. Therein, injection of fuel and reductant upstream of the close-coupled catalyst is adjusted based on an exhaust air-to-fuel ratio estimated downstream of the close coupled catalyst so as to maintain the air-to-fuel ratio at or around stoichiometry (e.g., slightly rich of stoichiometry) while generating ammonia for reducing of exhaust NOx species. In the absence of an underbody SCR catalyst, this ammonia can be stored on the underbody three-way catalyst due to the cooler exhaust temperatures at that location. During an onset of the VDE mode, pure air passes through one bank of the engine and the underbody three-way catalyst can oxidize the stored ammonia to NOx species and $N_2O$ using the oxygen in the fresh air. In addition, during the lean operation (that is, the VDE mode of operation), the three-way catalyst becomes oxidized which degrades its ability to reduce NOx species upon return to non-VDE/stoichiometric engine operation. In particular, the three-way catalyst is unable to reduce NOx species until the three-way has been sufficiently reduced and regenerated. To minimize the duration of this lost three-way catalyst function, significant enrichment can be used after exiting a VDE mode to quickly reduce the three-way catalyst. This enrichment not only adds a fuel penalty but also generates additional ammonia. The extra ammonia requires that the re-entry to a VDE mode be delayed to allow the ammonia to dissipate, otherwise the leftover ammonia would be oxidized to NOx and $N_2O$.

Herein, the specific configuration of an SCR catalyst integrated upstream of the three-way catalyst in the underbody emission control device addresses at least some of these issues. In particular, the specific position of the SCR catalyst downstream of the close-coupled three-way catalyst but upstream of the underbody three-way catalyst enables the SCR catalyst to store the ammonia generated by the close-coupled three-way catalyst and reduce storage of ammonia on the underbody three-way catalyst. It also reduces oxidation of the ammonia to NOx and $N_2O$ by the underbody three-way catalyst upon entry to VDE mode (lean operation). In addition, as elaborated at FIGS. 5A-B, the SCR catalyst can use the stored ammonia to reduce NOx upon return to non-VDE mode/stoichiometric engine operation. This provides sufficient time for the stoichiometric exhaust (or slightly rich exhaust) to reduce the close-coupled three-way catalyst. As also elaborated at FIGS. 5A-B, an engine controller may adjust a combustion exhaust air-to-fuel ratio during the cylinder reactivation based on an amount of ammonia stored on the SCR catalyst at the time of reactivation. The combustion air-to-fuel ratio may also be based on a change in the amount of ammonia stored in the SCR catalyst occurring during a selective cylinder deactivation immediately preceding the cylinder reactivation. Without ammonia in the SCR catalyst, at cylinder reactivation, the combustion air-to-fuel ratio may be shifted to be richer than stoichiometry for a duration until at least the close-coupled three-way catalyst is fully regenerated. In this way, the regeneration requirements for the close-coupled catalyst can be reduced depending on how much ammonia is stored in the SCR catalyst. By storing ammonia on the upstream underbody SCR catalyst during the preceding cylinder deactivation, the fuel penalty incurred during regeneration of the close-coupled three-way catalyst is reduced, improving fuel economy while also meeting NOx emissions requirements.

Figure 3:
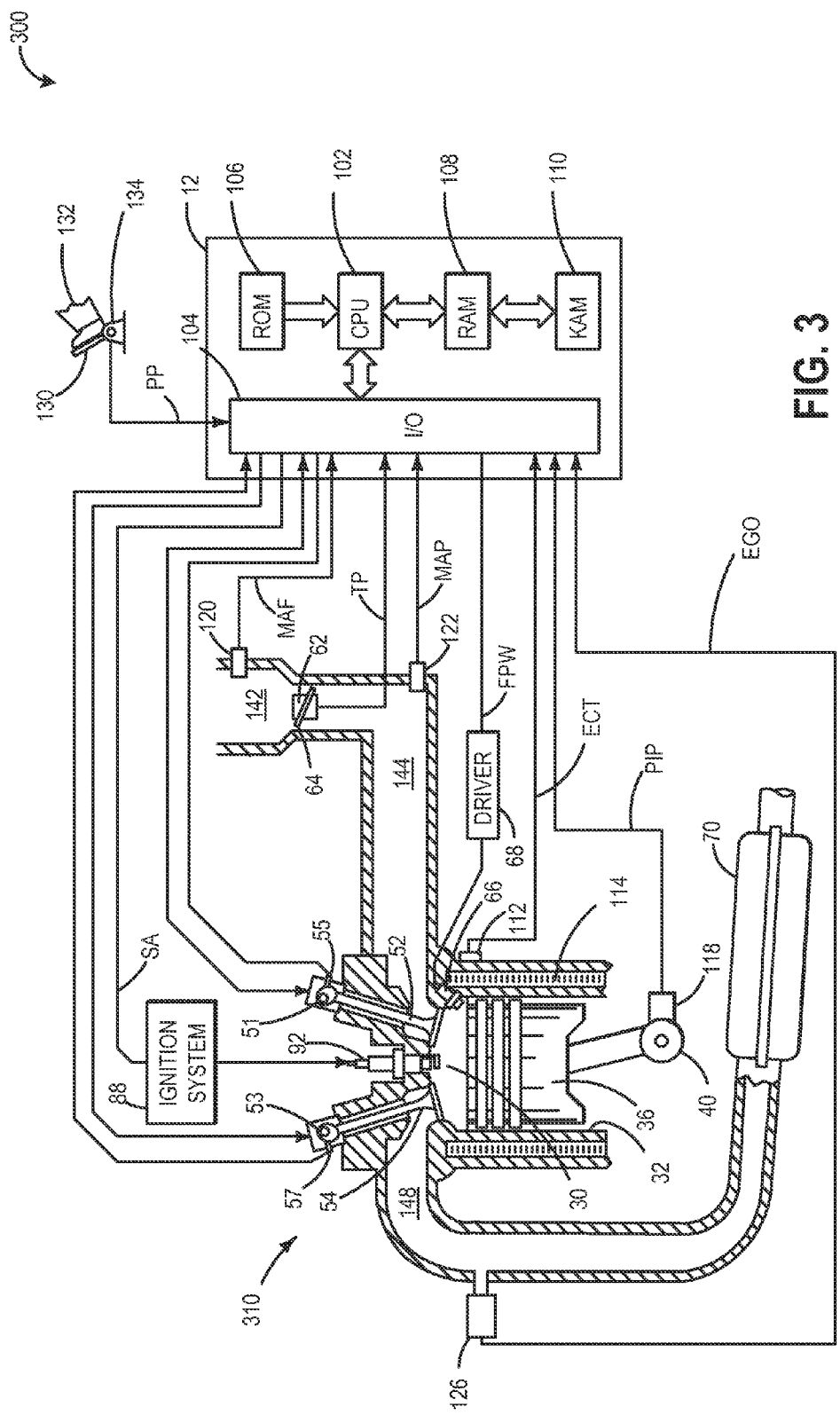
FIG. 3 depicts a partial engine view.

FIG. 3 is a schematic diagram showing one cylinder of multi-cylinder engine 310, which may be included in a propulsion system of an automobile. Engine 310 may be a variable displacement engine, such as engine 210 of FIGS. 2A-B and/or may be configured to be selectively deactivated responsive to idle-stop conditions, such as engine 10 of FIG. 1. Engine 10 may be controlled at least partially by a control system including controller 12 and by input from a vehicle operator 132 via an input device. In one example, the input device includes an accelerator pedal 130 and a pedal position sensor 134 for generating a proportional pedal position signal PP.

Combustion chamber 30 of engine 10 may include cylinder walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 144 via intake passage 142 and may exhaust combustion gases via exhaust passage 148. Intake manifold 144 and exhaust passage 148 can selectively communicate with combustion chamber 30 via respective intake valve 52 and exhaust valve 54. In some embodiments, combustion chamber 30 may include two or more intake valves and/or two or more exhaust valves. Exhaust camshaft 53 operates exhaust valve 54 in accordance with the profile of a cam located along the length of the exhaust camshaft. Intake camshaft 51 operates intake valve 52 in accordance with the profile of a cam located along the length of the camshaft. Exhaust cam position sensor 57 and intake cam position sensor 155 relay respective camshaft positions to controller 12.

Fuel injector 66 is shown coupled directly to combustion chamber 30 for injecting fuel directly therein in proportion to the pulse width of signal FPW received from controller 12 via electronic driver 68. In this manner, fuel injector 66 provides what is known as direct injection of fuel into combustion chamber 30. The fuel injector may be mounted in the side of the combustion chamber or in the top of the combustion chamber, for example. Fuel may be delivered to fuel injector 66 by a fuel system (not shown) including a fuel tank, a fuel pump, and a fuel rail. In some embodiments, combustion chamber 30 may alternatively or additionally include a fuel injector arranged in intake manifold 144 in a configuration that provides what is known as port injection of fuel into the intake port upstream of combustion chamber 30.

Intake passage 142 may include a throttle 62 having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. Intake passage 142 may include a mass air flow sensor 120 and a manifold air pressure sensor 122 for providing respective signals MAF and MAP to controller 12.

Ignition system 88 can provide an ignition spark to combustion chamber 30 via spark plug 92 in response to spark advance signal SA from controller 12, under select operating modes. Though spark ignition components are shown, in some embodiments, combustion chamber 30 or one or more other combustion chambers of engine 10 may be operated in a compression ignition mode, with or without an ignition spark.

Exhaust gas sensor 126 is shown coupled to exhaust passage 48 upstream of emission control device 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a NOx, HC, or CO sensor. Emission control device 70 is shown arranged along exhaust passage 48 downstream of exhaust gas sensor 126. Device 70 may be a three way catalyst (TWC), NOx trap, various other emission control devices, or combinations thereof. In some embodiments, during operation of engine 10, emission control device 70 may be periodically reset by operating at least one cylinder of the engine within a particular air/fuel ratio.

Controller 12 is shown in FIG. 3 as a microcomputer, including microprocessor unit 102, input/output ports 104, an electronic storage medium for executable programs and calibration values shown as read-only memory 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; vehicle brake 121; a profile ignition pickup signal (PIP) from Hall effect sensor 118 (or other type) coupled to crankshaft 40; throttle position (TP) from a throttle position sensor; and absolute manifold pressure signal, MAP, from manifold pressure sensor 122. Engine speed signal, RPM, may be generated by controller 12 from signal PIP. Manifold pressure signal MAP from a manifold pressure sensor may be used to provide an indication of vacuum, or pressure, in the intake manifold. Note that various combinations of the above sensors may be used, such as a MAF sensor without a MAP sensor, or vice versa. In one example, sensor 118, which is also used as an engine speed sensor, may produce a predetermined number of equally spaced pulses every revolution of the crankshaft.

Storage medium read-only memory 106 can be programmed with computer readable data representing instructions executable by microprocessor unit 102 for performing the methods described below as well as other variants that are anticipated but not specifically listed.

Controller 12 also receives signals from and provides control signals to a transmission (not shown). Transmission signals may include but are not limited to transmission input and output speeds, signals for regulating transmission line pressure (e.g., fluid pressure supplied to transmission clutches), and signals for controlling pressure supplied to clutches for actuating transmission gears.

As described above, FIG. 3 shows only one cylinder of a multi-cylinder engine, and that each cylinder may similarly include its own set of intake/exhaust valves, fuel injector, spark plug, etc.

Now turning to FIGS. 4A-B, method 400 shows an example routine for adjusting exhaust catalyst regeneration based on engine idle-stop operation. In particular, the method enables ammonia to be stored on a first exhaust catalyst when the engine is running so that the stored ammonia can be used during a subsequent engine restart from idle stop and a regeneration requirement of a third close-coupled exhaust catalyst at the restart can be reduced. In addition, the regeneration requirement of the second exhaust catalyst at the restart can be reduced.

At 402, the method includes estimating and/or measuring vehicle and engine operating conditions. These may include, for example, vehicle speed, engine speed, state of charge of a system battery, ambient temperature and pressure, engine temperature, crankshaft speed, transmission speed, fuels available, fuel alcohol content, etc. At 404, it may be determined if idle-stop conditions have been met. Idle-stop conditions may include, for example, the engine operating (e.g., carrying out combustion), the battery state of charge being above a threshold (e.g., more than 30%), vehicle speed being below a threshold (e.g., no more than 30 mph), no request for air conditioning being made, engine temperature (for example, as inferred from an engine coolant temperature) being above a threshold, no start being requested by the vehicle driver, driver requested torque being below a threshold, brake pedals being pressed, etc.

If any or all of the idle-stop conditions are met, then at 406, the controller may execute an automatic engine idle-stop operation and selectively deactivate the engine in response to the idle-stop. This may include shutting off fuel injection and/or spark ignition to the engine. For example, selectively deactivatable fuel injectors of selected cylinder may be deactivated and spark ignition to the selected cylinders may be discontinued. Upon deactivation, the engine may start spinning down to rest.

If idle-stop conditions are not met, at 405, the engine may continue to operate and not be shutdown. In particular, while the engine continues to run, the method includes flowing exhaust gas through a first, upstream exhaust catalyst and then a second, downstream exhaust catalyst of an exhaust underbody emission control device to store at least some ammonia on the first catalyst. As such, the first exhaust catalyst may be a first, SCR catalyst positioned upstream of (in a direction of exhaust flow), and integrated to, a second, three way exhaust catalyst in the underbody emission control device. In particular, the first SCR catalyst may be coupled to the second catalyst in a face-sharing brick arrangement such that an outer face of the first catalyst brick (that is, a face of the first brick via which exhaust leaves the first catalyst) is in face-to-face contact with an inner face of the second catalyst brick (that is, a face of the second brick via which exhaust enters the second catalyst).

While the routine depicts deactivating the engine in response to engine idle-stop conditions, in an alternate embodiment, it may be determined if a shutdown request has been received from the vehicle operator. In one example, a shutdown request from the vehicle operator may be confirmed in response to a vehicle ignition being moved to a key-off position. If an operator requested shutdown is received, the engine may be similarly deactivated by shutting off fuel and/or spark to the engine cylinders, and the engine may slowly spin down to rest.

At 408, an amount of ammonia stored on a first exhaust catalyst of the engine system may be estimated. As elaborated with reference to FIG. 6, the amount of ammonia stored on the first catalyst may depend on various factors that contribute to ammonia being produced and stored on the catalyst as well as various factors that contribute to ammonia being drawn out (e.g., consumed or dissipated) from the first exhaust catalyst. These include, in addition to a temperature, flow rate, and air-to-fuel ratio of exhaust flowing through the first catalyst, idle stop parameters including a duration of the most recent or immediately preceding idle stop (or expected duration of the idle stop) and a frequency of idle-stop operations over a drive cycle (e.g., a number of idle-stop operations performed since a last key-on event or a number of engine idle-stop events estimated over a duration of vehicle operation).

At 410, the estimated ammonia content on the first exhaust catalyst may be compared to a threshold and it may be determined if the ammonia content is higher than the threshold. If yes, then at 412, the controller may clear a rich regeneration flag. As such, during an engine restart from idle-stop, the controller may need to regenerate the third close-coupled exhaust catalyst (with a higher priority than the second exhaust catalyst) so that the catalyst is able to reduce exhaust NOx species. The controller may also need to regenerate the second exhaust catalyst (with a lower priority than the third three-way catalyst). However, a degree of regeneration required may be determined by the amount of ammonia stored during the preceding lean operation (herein, the idle-stop operation) on the first, exhaust catalyst. The larger the amount of ammonia that is stored on the first catalyst, the lower the regeneration requirement of the close-coupled catalyst will be. As elaborated herein, the controller may adjust regeneration of the third catalyst (as well as the second catalyst) during an engine restart from idle-stop based on the ammonia content of the first exhaust catalyst.

In particular, by clearing the rich regeneration flag at 412, the controller may indicate that there is sufficient ammonia stored on the first exhaust catalyst which can be used during a subsequent engine restart to reduce exhaust NOx without reducing or regenerating the close-coupled third exhaust catalyst. Consequently, additional fuel may not be required to regenerate the third exhaust catalyst. In comparison, if the ammonia content is lower than the threshold, then at 414, the routine includes setting a rich regeneration flag. Herein, the flag indicates that there is insufficient ammonia stored on the first exhaust catalyst, so the close-coupled three-way exhaust catalyst needs to be regenerated with rich exhaust to avoid $NO_x$ emissions during the restart. As such, if there is insufficient ammonia stored on the SCR catalyst, a rich regeneration is required to quickly reduce the close-coupled three-way catalyst so to avoid degraded exhaust NOx emissions.

After setting the rich regeneration flag at 414 or clearing the rich regeneration flag at 412, the method proceeds to 416, wherein it is determined if engine restart conditions have been met. As such, the engine restart conditions may include, for example, the engine being in idle-stop (e.g., not carrying out combustion), the battery state of charge being below a threshold (e.g., less than 30%), vehicle speed being above a threshold, a request for air conditioning being made, engine temperature being below a threshold, emission control device temperature being below a threshold (e.g., below a light-off temperature), driver requested torque being above a threshold, vehicle electrical load being above a threshold, brake pedals being released, accelerator pedal being pressed, etc. If restart conditions are not met, at 418, the engine may be maintained in the idle-stop status.

In comparison, if any or all of the restart conditions are met, without any restart being requested by the vehicle operator, at 420, the engine may be automatically restarted. This may include reactivating and cranking the engine. In one example, the engine may be cranked with starter motor assistance. Additionally, fuel injection and spark ignition to the engine cylinders may be resumed. In response to the automatic reactivation, the engine speed may start to gradually increase.

As explained above, during the engine restart, at least the third close-coupled exhaust catalyst may need to be regenerated so as to ensure catalytic function during engine running, and maintenance of exhaust emissions. As such, regenerating the third exhaust catalyst may include, during the engine restart, adjusting a fuel injection to the engine to provide an exhaust air-to-fuel ratio that is richer than stoichiometry, a degree of richness of the fuel injection based at least on the amount of ammonia stored on the first catalyst relative to the threshold amount responsive to the indication of a rich regeneration flag being set.

Thus if restart conditions are confirmed, then at 420, the controller may determine if a rich regeneration flag was previously set. That is, the controller may determine if a rich regeneration flag indicating a need for rich regeneration at engine restart from idle-stop was confirmed during the preceding engine idle-stop operation. If a rich regeneration flag was previously set, then at 422, the method includes restarting the engine from idle-stop conditions. The restarting may include resuming spark ignition and reactivating the cylinder fuel injectors. In addition, a fueling to the cylinders may be adjusted so that an exhaust air-to-fuel ratio has a higher rich bias. This allows the third exhaust catalyst to be regenerated at a relatively higher rich bias. As such, the higher rich bias may include operating the engine with an air-to-fuel ratio that is richer than stoichiometry.

In comparison, if a rich regeneration flag was not previously set, then at 424, the method includes restarting the engine from idle-stop conditions by resuming spark ignition and reactivating the cylinder fuel injectors. In addition, a fueling to the cylinders may be adjusted so that an exhaust air-to-fuel ratio has a lower rich bias. This allows the third exhaust catalyst to be regenerated at a relatively lower rich bias, including operating the engine with an air-to-fuel ratio that is at stoichiometry, or slightly richer than stoichiometry.

Adjusting the regeneration responsive to the regeneration flag and based on the ammonia content of the first catalyst may include, as the ammonia content of the first catalyst increases above a threshold, reducing a degree of richness of the regenerating fuel injection, and as the ammonia content of the first catalyst decreases below the threshold, increasing a degree of richness of the regenerating fuel injection. In some embodiments, the adjustment may also include adjusting a duration of the regeneration. For example, as the ammonia content of the first catalyst increases above the threshold, the controller may reduce a duration of regenerating the second catalyst with the rich fuel injection.

Herein, by clearing a rich regeneration flag responsive to the ammonia content of the first exhaust catalyst being higher than a threshold amount, a fuel penalty incurred to regenerate a third close-coupled exhaust catalyst during the engine restart from idle-stop can be reduced. Likewise, the fuel penalty incurred to regenerate a second exhaust catalyst during the engine restart can be reduced. In addition, the stored ammonia can be advantageously used by the first exhaust catalyst to reduce NOx species, thereby controlling NOx emissions while the second and third catalysts are regenerated.

Returning to FIGS. 4A-B, at 422 and 424, the engine is restarted with rich catalyst regeneration with higher or lower rich bias based on the stored ammonia content of the SCR catalyst so as to regenerate the (third) close-coupled three-way catalyst. From 422 and 424, the routine proceeds to 430 wherein it is determined if the close-coupled three-way catalyst (TWC) has been sufficiently regenerated. Upon confirmation that the close-coupled TWC is regenerated and active for NOx conversion, at 432, it may be determined if the vehicle operator is demanding high load operation. In one example, high load operation is confirmed in response to a hard acceleration. For example, the operator may apply hard on the accelerator pedal and the accelerator pedal position may be moved by a threshold distance. If a high load demand is confirmed, then at 434, the routine includes actively regenerating the second underbody three-way catalyst (TWC) with additional rich engine operation. That is, an air-to-fuel ratio may be adjusted to be richer than stoichiometry so as to quickly reduce the underbody TWC and make it active for NOx conversion. This allows the underbody TWC to supplement the NOx conversion of the close-coupled TWC so that the extra exhaust NOx generated during high load engine operation can be better addressed. Next, at 436, the routine determines if the second underbody TWC has been sufficiently regenerated. Upon confirmation, the routine proceeds to 440 wherein engine operation is returned to an air-to-fuel ratio that is slightly richer than stoichiometry (that is, a slight rich bias). If high load demand is not confirmed at 432, the routine proceeds to 438 wherein the second underbody TWC is not actively regenerated. Instead, the routine returns to the regular closed-loop control with a slight rich bias of air-to-fuel ratio. Herein, the slightly rich biased exhaust allows the second underbody three-way catalyst to be reduced slowly over time while the close-coupled TWC, which is now regenerated and active for NOx conversion, addresses the exhaust NOx. At 440, the routine then continues the slightly rich biased engine operation.

In one example, an engine system includes a first catalyst and a second catalyst integrated in an emission control device coupled to an exhaust manifold of the engine. The integrated emission control device may be an underbody emission control device. Each of the first and second catalysts may be positioned downstream of a third close-coupled exhaust catalyst. During a first engine restart from idle-stop, when an ammonia content of a first, upstream exhaust catalyst is higher than a threshold, a controller may operate the engine by injecting fuel with a first, lower rich bias to regenerate the third exhaust catalyst upstream of the first catalyst and possibly the second exhaust catalyst downstream of the first catalyst. In comparison, during a second engine restart from idle-stop, when an ammonia content of the first exhaust catalyst is lower than the threshold, the controller may operate the engine by injecting fuel with a second, higher rich bias to regenerate the second exhaust catalyst and the third exhaust catalyst. Herein, during each of the first and second engine restarts, the ammonia content of the first catalyst is based at least on a duration of an immediately preceding idle-stop. In addition, the ammonia content of the first catalyst may be further based on one or more engine operating conditions estimated during engine running prior to the idle-stop. The one or more conditions may include, for example, an exhaust gas temperature, an exhaust flow rate, engine speed, engine load, and exhaust air-to-fuel ratio. As such, during each of the first and second engine restarts, exhaust gas is flowed through the third catalyst, followed by the first catalyst and then the second catalyst before venting to atmosphere. This allows the ammonia generated at the third catalyst to be stored on the first catalyst rather than the second catalyst. In particular, where the first catalyst is an SCR catalyst and each of the second and the third catalysts are three-way catalyst, the generated ammonia can be stored on the SCR catalyst and the close-coupled three-way catalyst can be protected from unwanted oxidation during the lean engine operation (the idle-stop period).

In another example, an engine system comprises an engine that is selectively deactivatable responsive to idle-stop conditions, and an emission control device coupled to an engine exhaust manifold. The device includes a first, upstream catalyst in face-sharing contact with a second, downstream catalyst. Each of the first and second catalysts may be positioned downstream of a third close-coupled exhaust catalyst. The engine system further includes a control system with computer readable instructions for, during an engine restart from idle-stop, adjusting fuel injection to be richer than stoichiometry to regenerate at least the third catalyst (e.g., to regenerate the second and third catalysts), wherein a degree of richness is adjusted based on an ammonia content of the first catalyst. The ammonia content of the first catalyst at the engine restart is estimated based on the idle-stop with the ammonia content of the first catalyst at engine restart adjusted (e.g., increased or decreased) as a duration of the idle-stop increases. The adjusting includes, as the ammonia content of the first catalyst decreases, increasing a degree of richness of the fuel injection. The ammonia content of the first catalyst at engine restart may be further estimated based on a temperature of the emission control device with the ammonia content decreasing as the temperature decreases below a threshold (As such, the first catalyst may be an SCR catalyst and may have a higher ammonia storage content than the second catalyst. The engine controller may further include instructions for, prior to initiating an engine idle-stop, adjusting fuel injection to the engine to be richer than stoichiometry, a degree of richness adjusted responsive to an ammonia content of the first catalyst to maintain the ammonia content of the first catalyst above a threshold amount.

As such, based on the duration of the idle-stop, an amount of cooling of the first SCR catalyst may vary, which in turn affects the catalyst's ammonia storage capacity. For example, cooling of the SCR catalyst may increase the catalyst's ammonia storage capacity until a threshold temperature is reached, allowing it to store more ammonia. Thus, if ammonia was stored on the first catalyst, as the temperature of the first catalyst falls and the vehicle is turned off, stored ammonia may remain on the SCR catalyst and be available at the next engine cold start. Additionally, when exhaust is flowing through the emission control device, it carries heat away from the catalysts, allowing the ammonia storage capacity of the SCR catalyst to be increased. Then, when the engine is stopped during the idle-stop, the SCR catalyst temperature may temporarily increase, causing the SCR catalyst to oxidize some of the stored ammonia to nitrogen or NO using the oxygen pumped in the 2-3 engine revolutions after fuel shut-off.

Herein, in anticipation of potential catalyst regeneration required during an engine restart from idle-stop, the controller may pre-charge the first exhaust catalyst while factoring in ammonia losses from the first catalyst that may be incurred during the idle-stop due to air flow through the engine and due to ammonia oxidation and ammonia release caused by temperature increases at the exhaust emission control device. By pre-charging the first exhaust catalyst while an engine is running and before an engine idle stop is commenced, the controller may not only protect the second exhaust catalyst from being loaded with ammonia during the idle-stop, but may also further reduce the regeneration requirement of the third close-coupled catalyst at the restart while keeping NOx emissions under control.

In this way, issues related to exhaust catalyst regeneration and exhaust emissions arising during idle-stop events can be better addressed. By adjusting an exhaust air-to-fuel ratio before catalyst regeneration is required to load an underbody exhaust SCR catalyst with ammonia, ammonia loading of an underbody three-way catalyst can be reduced. By using the stored ammonia to reduce NOx species during a subsequent engine restart from idle-stop, exhaust NOx may be addressed by the SCR catalyst while an upstream close-coupled three-way catalyst recovers its reductive capability. By using the stored ammonia during the subsequent engine restart from idle-stop, a fuel penalty incurred in regenerating the close-coupled three-way catalyst can be reduced.

Figure 5A:
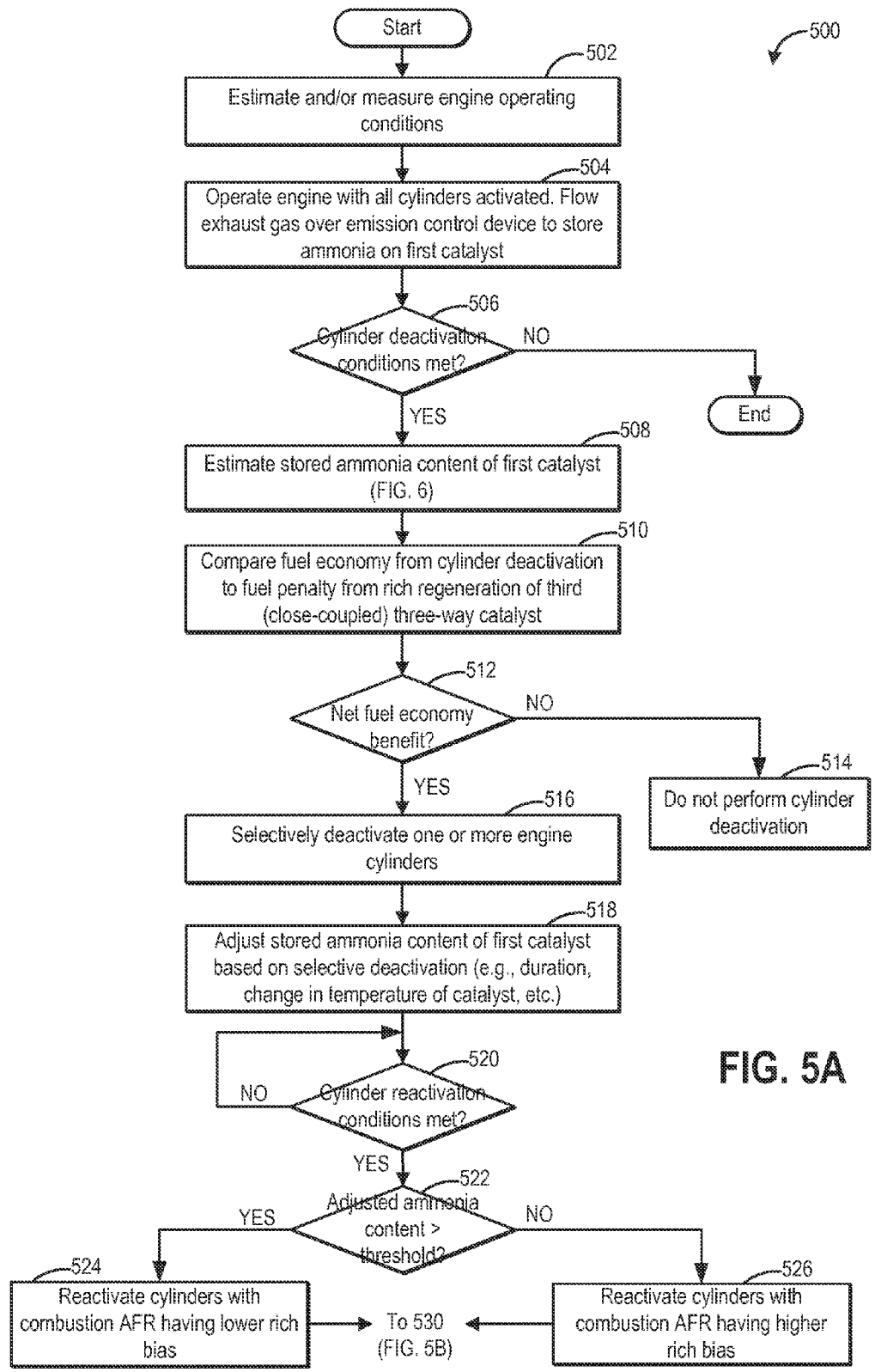
FIGS. 5A-B illustrate an example method for adjusting regeneration of a second and third exhaust catalyst during a switch from VDE mode to non-VDE mode of engine operation based on an amount of ammonia retained on a first exhaust catalyst during the VDE mode.
Figure 5B:
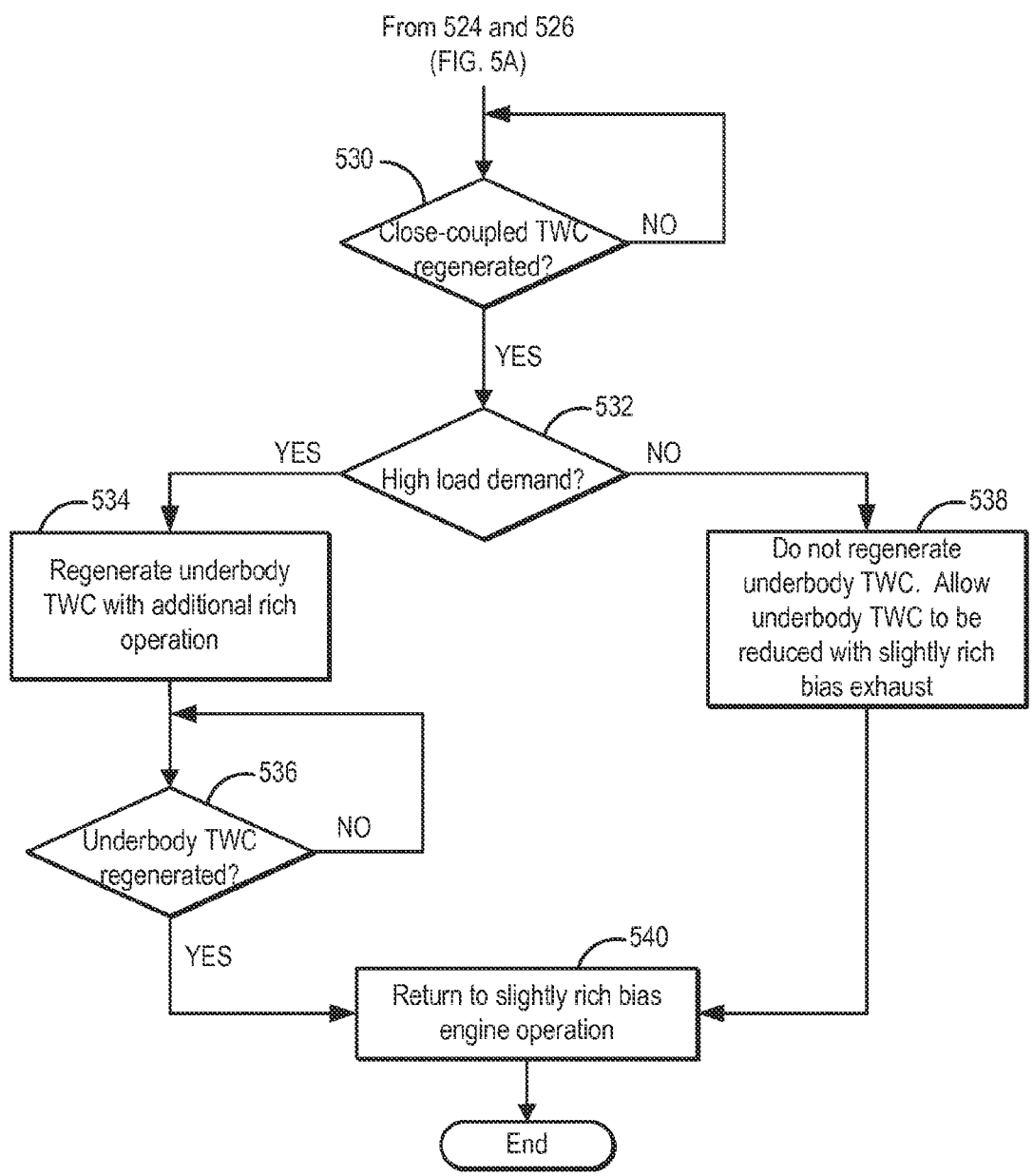

Now turning to FIGS. 5A-B, method 500 shows an example routine for adjusting exhaust catalyst regeneration based on selective cylinder deactivation operations in a VDE engine. In particular, the method enables ammonia to be stored on a first exhaust catalyst when all engine cylinders are activated so that the stored ammonia can be used during a subsequent engine reactivation from VDE mode and a regeneration requirement of a third close-coupled exhaust catalyst upstream of the first SCR catalyst and possibly a second underbody exhaust catalyst coupled downstream of the SCR catalyst, at the switch from VDE to non-VDE mode can be reduced.

At 502, the method includes estimating and/or measuring vehicle and engine operating conditions. These may include, for example, vehicle speed, engine speed, state of charge of a system battery, ambient temperature and pressure, engine temperature, crankshaft speed, transmission speed, fuels available, fuel alcohol content, etc.

At 504, the engine may be operated with all cylinders activated and combusting. While all the engine cylinders are running, combusted exhaust gas may be flowed over an underbody exhaust emission control device before being vented to the atmosphere so as to store ammonia on a first exhaust catalyst of the emission control device. The first exhaust catalyst may be coupled upstream of a second exhaust catalyst in the emission control device wherein the second catalyst is in face sharing contact with, and integrated together with, the first catalyst in the underbody emission control device. In one example, the first catalyst is an SCR catalyst while the second catalyst is a three-way catalyst. In addition, each of the first and second catalysts may be positioned in an engine exhaust manifold downstream of a third close-coupled three-way catalyst. Thus, while all the cylinders are combusting, at least some ammonia is stored in the first catalyst. By storing the generate ammonia on the first SCR catalyst, ammonia storage on the second catalyst can be reduced. As explained below, this prevents the second three-way catalyst from oxidizing ammonia to NO or $N_2O$ during the VDE mode, and getting oxidized in the event of a shift from VDE to non-VDE mode. In addition, it reduces NOx generation at the three-way catalyst during the shift (that would arise from oxidation of the ammonia stored on the three-way catalyst).

In some embodiments, while the engine is running with all cylinders active, and prior to any selective deactivation of engine cylinders, a controller may operate the engine with a combustion air-to-fuel ratio adjusted to be richer than stoichiometry for a duration to actively raise the ammonia content on the first catalyst. For example, cylinder combustion may be performed at richer than stoichiometry for a duration until the ammonia content stored in the first exhaust catalyst is higher than a threshold amount.

At 506, it may be determined if cylinder deactivation conditions have been met. In particular, based on the estimated operating conditions, the routine may determine an engine mode of operation (e.g., VDE or non-VDE). As one example, cylinder deactivation conditions may be confirmed when torque demand is less than a threshold. As such, if cylinder deactivation conditions are not met at 506, the routine may end with the engine operating with all cylinders firing.

At 508, an amount of ammonia stored on the first exhaust catalyst may be estimated. As such, prior to the cylinder deactivation, while all engine cylinders are combusting, ammonia may have been stored on the first exhaust catalyst. As elaborated with reference to FIG. 6, the amount of ammonia stored on the first catalyst may depend on various factors that contribute to ammonia being produced and stored on the catalyst as well as various factors that contribute to ammonia being drawn out (e.g., consumed or dissipated) from the first exhaust catalyst. These include, for example, a temperature, flow rate, and air-to-fuel ratio of exhaust flowing through the first catalyst prior to the cylinder deactivation.

At 510, the controller may compare an estimated fuel economy incurred from cylinder deactivation with an estimated fuel penalty incurred from regeneration of the second exhaust catalyst. As such, cylinder deactivation at low engine loads reduces engine pumping losses and friction losses, leading to a reduction in fuel consumption. The controller may estimate a fuel economy from the VDE operation based on the reduction in pumping losses and friction losses expected. In addition, the fuel economy estimate may be based on an expected duration of operation in the VDE mode. However, the lean engine operation resulting from the cylinder deactivation can oxidize the third close-coupled exhaust catalyst which then has to be regenerated using a rich fuel injection during the subsequent reactivation. The controller may estimate a fuel penalty incurred from the rich regeneration based on a duration of VDE operation and a flow rate of air through the deactivated cylinders. For example, if the engine in operated in the VDE mode for a shorter duration, the penalty incurred in regeneration of the close-coupled three-way catalyst may outweigh the fuel saved during the VDE mode. As another example, if the engine is operated in the VDE mode for a longer duration, the fuel saved during the VDE mode may outweigh the penalty incurred in regeneration of the close-coupled three-way catalyst.

At 512, based on the comparison, it may be determined if there is a net fuel economy benefit. For example, it may be determined if the fuel expected to be saved by operating in the VDE mode is more than the fuel expected to be consumed when regenerating the close-coupled exhaust catalyst upon shift to non-VDE mode. If a net fuel economy benefit is not confirmed, then at 514, the routine includes not performing cylinder deactivation (even though VDE conditions are present). Herein, it may be determined that more fuel would be consumed in regenerating the close-coupled catalyst oxidized during a VDE mode of operation than fuel saved by operating in the VDE mode.

If a net fuel economy benefit is confirmed, then at 516, the routine includes selectively deactivating one or more selected engine cylinders. This may include selectively deactivating fuel to the one or more selected engine cylinders so that fuel is not combusted in the cylinders. However, air may continue to flow through the deactivated cylinders. Alternatively, the valves of the cylinders may also be closed so as to reduce the amount of air directed through the deactivated cylinders.

At 518, the routine includes adjusting the estimated stored ammonia content of the first exhaust catalyst (as previously estimated at 508) during the selective deactivation based on selective deactivation parameters. These may include, for example, a duration of selective deactivation, a number of cylinder deactivated (or a number of cylinders remaining active), and a change in catalyst temperature due to air flow and lack of combustion in the selected cylinders during the deactivation. As such, a change in the ammonia content may occur during the selective deactivation based at least on a change in temperature of the first exhaust catalyst due to the air flowing there-through. In particular, as the duration increases and the emission control device rises to a temperature over 300° C. (due to no exhaust flowing through the catalyst to take away exhaust heat), the stored ammonia content may decrease due to oxidation of the ammonia and due to release of stored ammonia from the catalyst due to a temperature increase at the emission control device. Likewise, during a VDE operation, less $NH_3$ will be stored at the SCR catalyst since there is none being produced. Thus, the adjusting of the estimated stored ammonia content may include decreasing the ammonia content stored in the first exhaust catalyst as the temperature of the first exhaust catalyst decreases below a threshold temperature. If the temperature of the first catalyst remains above the threshold temperature following cooling over the idle-stop duration, the catalyst may have an increased ammonia storage capacity and more ammonia may be stored there-on. In addition, if the SCR catalyst temperature is above a temperature at which the catalyst is hot enough to oxidize stored ammonia to NO and nitrogen, the estimated ammonia content may be decreased to compensate for ammonia losses incurred from oxidation.

In some embodiments, the ammonia content may also change during the selective deactivation based on the combustion conditions of the active engine cylinders. For example, during the selective deactivation when the engine is in the VDE mode, the active engine cylinders may be operated richer than stoichiometry (for at least a duration) so as to increase the amount of ammonia stored on the first exhaust catalyst. Herein, the first catalyst may be pre-charged with ammonia in anticipation of third (close-coupled) catalyst regeneration required during the subsequent shift back to a non-VDE mode. In addition, the first catalyst may be pre-charged with ammonia in anticipation of regeneration requirements of the second catalyst during high load conditions. In one example, the change in ammonia content may include an increase in the ammonia content stored in the first exhaust catalyst as a cylinder combustion air-to-fuel ratio of the active engine cylinders becomes richer than stoichiometry.

It will be appreciated that the increase in ammonia content due to non-VDE cylinders operating richer than stoichiometry is applicable to embodiments where the engine banks have a common underbody emission control device, as shown in FIG. 2B, rather than in embodiments where the engine banks have dedicated underbody emission control devices with respective underbody SCR catalysts.

Next, at 520, it may be determined if cylinder reactivation conditions have been met and if the engine can/should be shifted back to a non-VDE mode of operation. Cylinder reactivation conditions may be confirmed in response to, for example, a driver torque demand being higher than a threshold level (e.g., during a tip-in). As another example, cylinder reactivation conditions may be confirmed after the engine has been operated with cylinder deactivation (that is, in the VDE mode) for a defined duration. As such, the engine may continue operating in the VDE mode with one or more engine cylinders selectively deactivated until the engine reactivation conditions are met.

Upon confirmation of reactivation conditions, at 522, the adjusted ammonia content of the first exhaust catalyst may be retrieved and compared to a threshold amount. As such, at 524 and 526, the controller may reactivate the engine cylinders and resume combustion in all the cylinders with a combustion air-to-fuel ratio adjusted based on the stored ammonia content. In particular, at 522 it may be determined if the adjusted ammonia content of the first exhaust catalyst is higher than a threshold amount. This includes determining if the ammonia content of the first exhaust catalyst that was initially estimated at 508 and further adjusted based on the VDE mode of operation at 518 is higher than the threshold amount. If yes, then at 524, the controller may reactivate the engine cylinders to switch engine operation back to the non-VDE mode with engine combustion adjusted to an air-to-fuel ratio having a lower rich bias. Herein, the higher ammonia content indicates that there is sufficient ammonia stored on the first exhaust catalyst that can be used during the switch back to the non-VDE mode to reduce exhaust NOx. Upon returning to the non-VDE mode, the close-coupled (third) TWC and the underbody (second) TWC may be reduced by the use of a slightly rich exhaust. Consequently, additional fuel may not be required to regenerate the third close coupled exhaust catalyst and the engine can be operated with a lower rich bias. The lower rich bias may include operating the cylinders at stoichiometry or slightly richer than stoichiometry.

In comparison, if the adjusted ammonia content of the first exhaust catalyst is lower than the threshold, then at 526, the controller may reactivate the engine cylinders to switch engine operation back to the non-VDE mode with engine combustion adjusted to an air-to-fuel ratio having a higher rich bias. Herein, the lower ammonia content that there is insufficient ammonia stored on the first exhaust catalyst and additional fuel is required during the switch back to the non-VDE mode to reduce exhaust NOx. Consequently, additional fuel is required to regenerate the third exhaust catalyst and the engine can be operated with a higher rich bias. The higher rich bias may include operating the cylinders richer than stoichiometry with a degree of richness adjusted based on a regeneration state of the third catalyst and/or based on the difference of the ammonia content of the first catalyst from the threshold amount.

Thus, at 524 and 526, the engine cylinders are reactivated with rich catalyst regeneration with higher or lower rich bias based on the stored ammonia content of the SCR catalyst so as to regenerate the (third) close-coupled three-way catalyst. From 524 and 526, the routine proceeds to 530 wherein it is determined if the close-coupled three-way catalyst (TWC) has been sufficiently regenerated. Upon confirmation that the close-coupled TWC is regenerated and active for NOx conversion, at 532, it may be determined if the vehicle operator is demanding high load operation. In one example, high load operation is confirmed in response to a hard acceleration. For example, the operator may apply hard on the accelerator pedal and the accelerator pedal position may be moved by a threshold distance. If a high load demand is confirmed, then at 534, the routine includes actively regenerating the second underbody three-way catalyst (TWC) with additional rich engine operation. That is, an air-to-fuel ratio may be adjusted to be richer than stoichiometry so as to quickly reduce the underbody TWC and make it active for NOx conversion. This allows the underbody TWC to supplement the NOx conversion of the close-coupled TWC so that the extra exhaust NOx generated during high load engine operation can be better addressed. Next, at 536, the routine determines if the second underbody TWC has been sufficiently regenerated. Upon confirmation, the routine proceeds to 540 wherein engine operation is returned to an air-to-fuel ratio that is slightly richer than stoichiometry (that is, a slight rich bias). If high load demand is not confirmed at 532, the routine proceeds to 538 wherein the second underbody TWC is not actively regenerated. Instead, the routine returns to the regular closed-loop control with a slight rich bias of air-to-fuel ratio. Herein, the slightly rich biased exhaust allows the second underbody three-way catalyst to be reduced slowly over time while the close-coupled TWC, which is now regenerated and active for NOx conversion, addresses the exhaust NOx. At 540, the routine then continues the slightly rich biased engine operation.

As one example, an engine controller may selectively deactivate one or more engine cylinders while flowing exhaust gas through each of a first and second exhaust catalyst. Then, during a first reactivation of the cylinders, when an ammonia content of the first exhaust catalyst is lower than a threshold, an engine combustion air-to-fuel ratio may be adjusted to be richer than stoichiometry with a first, higher rich bias. Then, during a second reactivation of the cylinders, when the ammonia content of the first exhaust catalyst is higher than a threshold, the controller may adjust the engine combustion air-to-fuel ratio to be richer than stoichiometry with a second, lower rich bias. In this way, during each of the first and second reactivations back to a non-VDE mode, exhaust gas is flowed through the first catalyst and then the second catalyst before venting to atmosphere. This allows the generated ammonia to be stored on the first catalyst rather than the second catalyst. In particular, where the first catalyst is an SCR catalyst and the second catalyst is a three-way catalyst, the generated ammonia can be stored on the SCR catalyst and oxidation of ammonia to NO or $N_2O$ at the second catalyst during the lean engine operation (e.g., VDE mode of operation) can be reduced.

In some embodiments, while selectively deactivating one or more engine cylinders, the controller may flow exhaust gas through each of the first and second exhaust catalyst while adjusting fuel injection of the active engine cylinders to be richer than stoichiometry. This is done so as to raise the ammonia content of the first catalyst (pre-emptively) above a threshold amount while the engine is operating in the VDE mode and before the engine is shifted back to the non-VDE mode. For example, an engine controller may combust fuel in a first group of cylinders on a first engine bank at a first air-to-fuel ratio while deactivating fuel injection to a second group of cylinders on a second engine bank. Herein the first air-to-fuel ratio is adjusted to raise an ammonia content of the first exhaust catalyst above a threshold before reactivating fuel injection to the second group of cylinders. The first exhaust catalyst may be coupled upstream of, and integrated with, a second exhaust catalyst in an underbody engine exhaust emission control device. In particular, the first exhaust catalyst may be an SCR catalyst and the second exhaust catalyst. The first air-to-fuel ratio may be richer than stoichiometry with a degree of richness of the first air-to-fuel ratio adjusted based on a difference between the ammonia content of the first exhaust catalyst from the threshold. In particular, the degree of richness of the rich air-to-fuel ratio may be increased as the difference between the ammonia content of the first exhaust catalyst and the threshold increases. Additionally, after reactivating fuel injection to the second group of cylinders, the controller may combust fuel in each of the first and second group of cylinders at a second air-to-fuel ratio that is based on the ammonia content of the first exhaust catalyst and a regeneration state of the second exhaust catalyst at the time of return to non-VDE mode. Herein, the second air-to-fuel ratio may be at or richer than stoichiometry and a degree of richness of the second air-to-fuel ratio may be based on a duration of the deactivation of fuel injection and a regeneration state of the close-coupled third three-way exhaust catalyst at the reactivation of fuel injection.

Herein, in anticipation of potential catalyst regeneration required during an engine operation shift back from VDE mode to non-VDE mode, the controller may pre-charge the first exhaust catalyst while factoring in ammonia losses from the first catalyst that may be incurred during the cylinder deactivation (operation in VDE mode) due to air flow through the engine and temperature changes at the exhaust emission control device as well as oxidation of the stored ammonia to NO or $N_2$. By pre-charging the first exhaust catalyst while an engine is running and before an engine reactivation to non-VDE mode is commenced, the controller not only protects the second exhaust catalyst from being loaded with ammonia during the VDE mode, but may also further reduce the regeneration requirement of the close-coupled three-way exhaust catalyst at the time of switch back to non-VDE while keeping NOx emissions under control.

Figure 6:
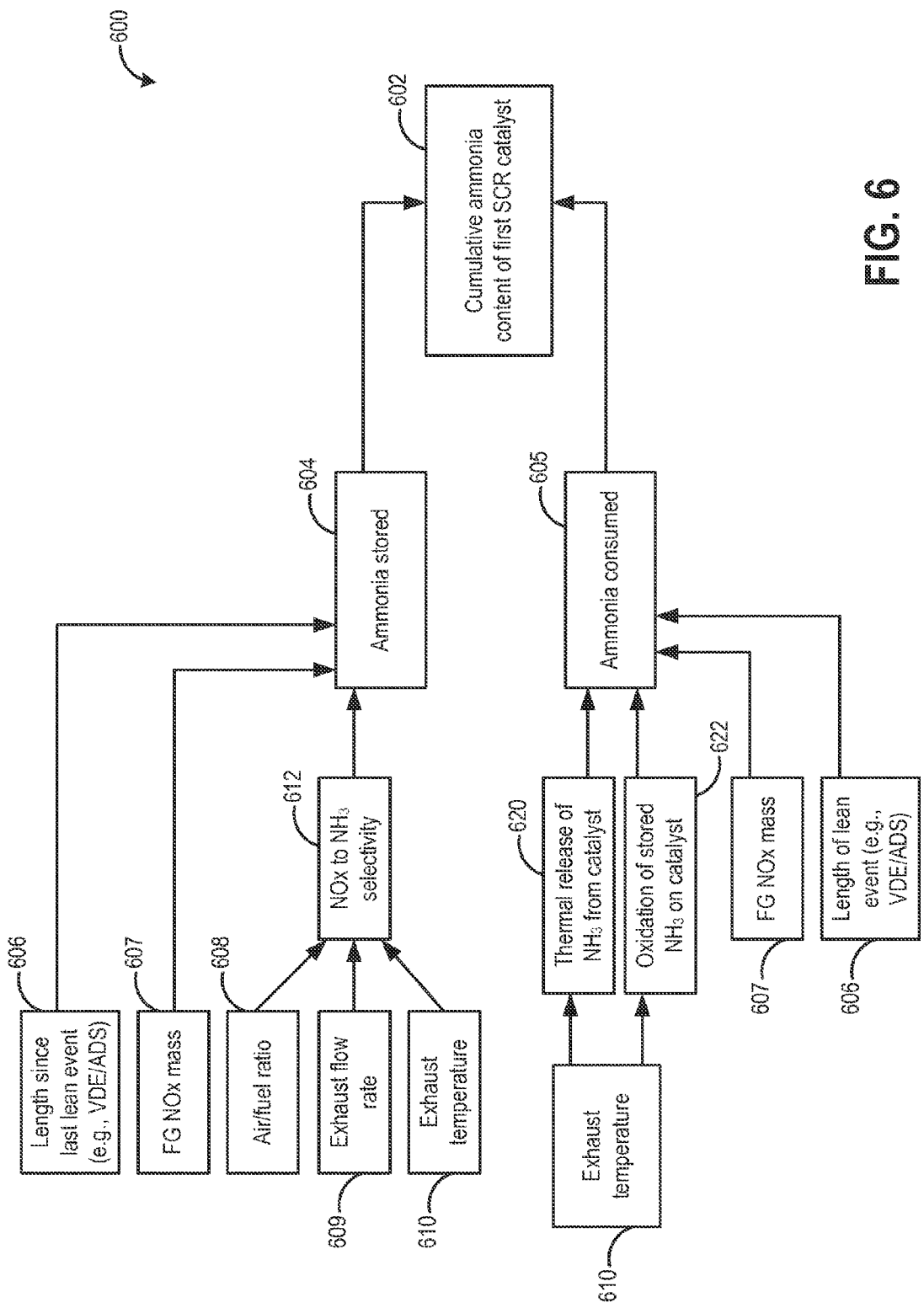
FIG. 6 illustrates an example block diagram that may be used to estimate an ammonia content of the first exhaust catalyst.
Figure 7:
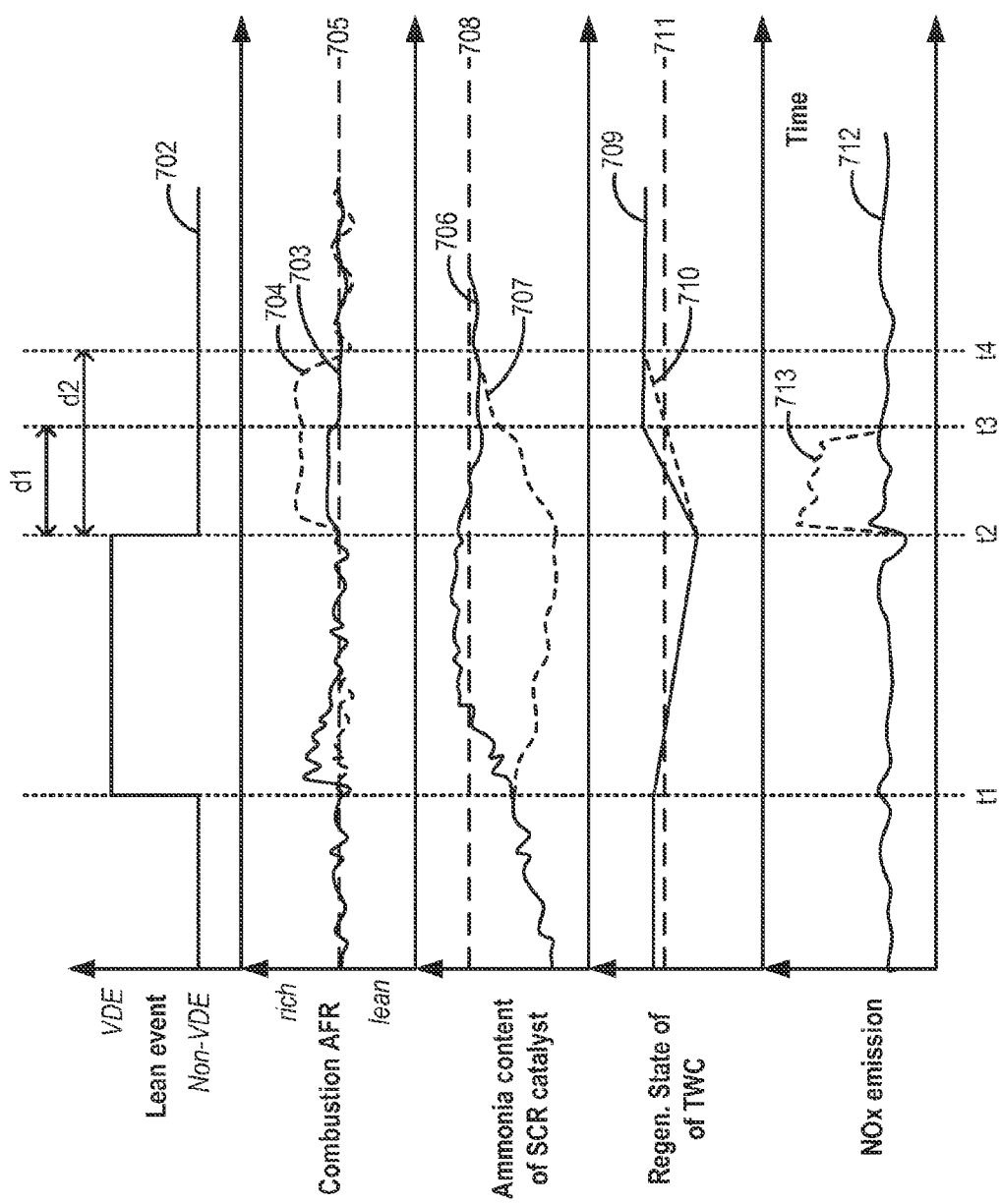
FIG. 7 illustrates an example adjustment to an exhaust air-to-fuel ratio during an engine regeneration operation following a lean engine event.

Now turning to FIG. 6, it shows a block diagram 600 for estimating an ammonia content of the first (SCR) exhaust catalyst. An engine controller may be configured to use a model, such as the model depicted at 600, to continuously estimate and update an ammonia content of the SCR catalyst during lean engine events, such as during an engine idle-stop or while operating the engine in a VDE mode, as well as non-lean events (such as during stoichiometric or slightly rich engine operation).

A cumulative ammonia content of the first SCR catalyst 602 may be estimated based on a comparison of the ammonia stored 604 (or produced) during stoichiometric or slightly rich engine operations relative to the ammonia consumed 605 under the given operating conditions of the lean event. As such, the ammonia produced may be based on various factors that are determined by the nature of the lean event. In one example, the controller may be configured to set a different flag based on which type of lean event is occurring and accordingly adjust the factors assessed in the estimation of ammonia produced to ammonia consumed. For example, the controller may set a first flag when the lean event is an engine idle-stop event and may estimate the ammonia produced before the idle-stop and the ammonia during the idle-stop consumed based on idle-stop parameters. As another example, the controller may set a second, different flag when the lean event is an engine VDE mode of operation and may estimate the ammonia produced (by the non-VDE bank operating at a slightly rich air-to-fuel ratio) and the ammonia consumed based on VDE mode parameters.

The ammonia stored 604 and ammonia consumed 605 may be based on a length since the last lean event 606 as well a duration of the most recent lean event. For example, where the lean event is a VDE mode of operation, it may be determined how long a most recent (or current) VDE mode is running for as well as a duration since a last switch from VDE mode to non-VDE mode. As such, a duration since a last switch from VDE mode to non-VDE mode may also be estimated based on a duration of the most recent non-VDE mode of operation. As the duration between VDE modes of operation increases, the amount of ammonia produced may increase and the amount of ammonia consumed may decrease. In particular, the longer the duration of engine operation at stoichiometry (or richer than stoichiometry), the larger the amount of ammonia stored 604 and the smaller the amount of ammonia used 605.

In an alternate example, where the lean event is an engine idle-stop event, it may be determined how long a most recent (or current) engine idle-stop ran for as well as a duration since a last restart from idle-stop conditions. In some embodiments, where the engine may have performed multiple idle-stops in a short duration of time (e.g., in busy traffic conditions), the controller may determine a frequency of the idle-stops or a number of idle-stop events that have occurred in a threshold duration (or since a last key-on event). In another example, the controller may determine a number of idle-stops, as well as a cumulative duration of the idle-stops over a drive cycle including from a key-on event to a key-off event. As the duration between consecutive idle-stop events increases, the amount of ammonia produced may also increase and the amount of ammonia consumed may decrease. In particular, the longer the duration of engine operation between idle-stops, where the engine is operating at stoichiometry (or richer than stoichiometry), the larger the amount of ammonia stored 604 and the smaller the amount of ammonia consumed 605.

Ammonia stored 604 and ammonia consumed 605 is also affected by the feedgas (FG) NOx mass 607. As such, the ammonia stored on the SCR catalyst is used by the SCR catalyst to reduce exhaust NOx species, however the ammonia is produced at the close-coupled three-way catalyst. Thus, as the feedgas NOx mass 607 increases, the amount of ammonia that can be produced by the close-coupled three-way catalyst increases and the amount of ammonia stored 604 on the SCR catalyst may correspondingly increase and the amount of ammonia consumed 605 may decrease. However, the amount of ammonia consumed upon re-entry to a non-VDE mode will also be increased. In one example, the controller may determine the FG NOx mass rate from a look-up table based on engine speed, load, EGR percentage, ambient temperature, etc. For example, look-up tables can be used to estimate the feedgas NOx level based on the listed parameters by mapping the NOx level from the engine at different engine speeds, loads, EGR percentages, etc. Alternatively, a NOx sensor may be used to measure the NOx in the feedgas, though they may be more expensive. Based on calculated concentration and flow rate (e.g., from a mass flow meter), the grams of ammonia stored on the SCR catalyst can be determined.

Ammonia stored 604 is also affected by the conditions of exhaust flowing through the emission control device. These include the exhaust air/fuel ratio 608, the exhaust flow rate 609, and the exhaust temperature 610. As such, as the combustion air/fuel ratio is enriched and as the exhaust flow rate is increased, more ammonia is generated by the upstream close-coupled three-way catalyst and stored on the downstream SCR catalyst. Once the close-coupled three-way catalyst is reduced, it can convert a lot of the feedgas NOx to ammonia even with only a slightly rich air-to-fuel ratio. The main advantage of the richer air-to-fuel ratio is that it reduces the three-way catalyst faster so that ammonia can be generated sooner. Thus, as the air/fuel ratio becomes richer than stoichiometry, the amount of ammonia stored on the SCR catalyst may increase. Likewise, as the exhaust flow rate increases, more ammonia is stored on the SCR catalyst. In comparison, as the exhaust temperature increases, ammonia is desorbed from the SCR catalyst. In one example, the SCR catalyst absorbs and stores ammonia at exhaust temperatures at or below 350-400° C. while the stored ammonia is desorbed at higher exhaust temperatures. In particular, the ammonia storage capacity of the SCR catalyst drops to very low levels above 400° C., and particularly above 450° C. Thus, most of the ammonia stored on the SCR catalyst will be released if the temperature exceeds 400° C.

The exhaust temperature also affects the amount of ammonia consumed 605 due to thermal release of ammonia from the catalyst 620 at higher exhaust temperatures as well as oxidation of stored ammonia 622 on the catalyst to nitrogen (or NO) due to the exhaust temperature increases. However, the amount of ammonia stored from the exhaust gas is also affected by the NOx to ammonia ($NH_3$) selectivity 612 of the close-coupled three-way catalyst. The selectivity, in turn, is determined based on catalyst conditions. These include, for example, the air-to-fuel ratio, the flow rate, and the exhaust temperature.

A controller may continually update factors 606-622 based on engine operating conditions (e.g., engine speed, load, EGR percentage, ambient temperature, etc.) to compare the ammonia produced and the ammonia consumed on the first exhaust catalyst and determine a net ammonia content on the exhaust catalyst. If the amount of ammonia stored on the SCR catalyst is sufficiently high, then during a return to engine operation from a lean event (e.g., during a shift back to non-VDE mode from VDE mode of operation, or during an engine restart from idle-stop), a controller may reduce the rich bias of a fuel injection used to regenerate the close-coupled three-way catalyst positioned upstream of the SCR catalyst. In addition, during high engine load operations, where NOx conversion at the second catalyst may be required, the rich bias of the fuel injection may also be used to regenerate the second catalyst positioned downstream of the SCR catalyst.

An example engine regeneration operation following a lean engine event is now elaborated with reference to FIG. 7. In particular, map 700 shows example air-to-fuel ratio adjustments performed to store ammonia on an upstream exhaust underbody SCR catalyst to reduce the fuel penalty incurred in regenerating an upstream three-way catalyst and/or a downstream exhaust underbody three-way catalyst. Map 750 depicts a shift between VDE and non-VDE modes at plot 702 and changes in a combustion air-to-fuel ratio (AFR) at plots 703, 704 relative to stoichiometry 705. Changes in the ammonia content of the SCR catalyst are shown at plots 706, 707 while corresponding changes in the regeneration state of the close-coupled three-way catalyst (TWC) are shown at plots 709, 710. Changes in an exhaust NOx level are shown at plots 712, 713. All changes are shown over time (along the x-axis).

Prior to t1, the engine may be operating in the non-VDE mode (plot 702) with all engine cylinders active and combusting substantially at stoichiometry 705 (plot 704, solid line). As the engine operates at stoichiometry, an ammonia content of the SCR catalyst may gradually increase (plot 706, solid line), however, the ammonia content may still be lower than a threshold amount 708. Prior to t1, the ammonia content of the SCR catalyst may be lower than the threshold and the three-way catalyst (TWC) may be in a higher state of regeneration, that is, it may not require further regeneration.

At t1, due to a change in engine operating conditions (e.g., during an extended tip-out), the engine may shift to a VDE mode of operation (plot 702) with one or more engine cylinders (e.g., on a selected bank) being selectively deactivated. Additionally, a combustion air-to-fuel ratio of the active engine cylinders may be adjusted to be slightly richer than stoichiometry (plot 703, solid line) for a duration until the ammonia storage content (plot 706) of the SCR catalyst is raised above threshold amount 708. Once the SCR catalyst has been charged with ammonia, the active engine cylinders may return to stoichiometric operation (plot 703). Herein, by pre-charging the SCR catalyst with ammonia, exhaust NOx can be reduced while the under-body three-way catalyst is being reduced upon return to the non-VDE mode. On engines with dual exhaust streams (such as shown at FIG. 2A), as well as in-line engines, the SCR catalyst may need to be charged with ammonia prior to going into the VDE mode. For engines with a common exhaust stream (such as shown at FIG. 2B), ammonia is made by the firing cylinders while cylinders on the other bank are in the VDE mode.

As such, the VDE mode may be continued until cylinder reactivation conditions are met at t2. Between t1 and t2, due to air flowing through the inactive bank, a regeneration state of the close-coupled TWC may decrease (plot 709). That is, by the time a shift to non-VDE mode is requested, the close-coupled TWC may need to be regenerated. However, due to the presence of the downstream SCR catalyst, most of the generated ammonia may be stored at the SCR catalyst and very little ammonia may be retained on and oxidized on the downstream underbody TWC.

At t2, in response to cylinder reactivation conditions being met (plot 702), engine operation may be shifted back to non-VDE mode. In addition, to regenerate the TWC, a combustion air-to-fuel ratio (plot 703) may be enriched for a first, shorter duration d1 to bring the regeneration state of the TWC (plot 709) above a threshold state 711. The degree of richness of the rich fuel injection is adjusted based on the ammonia storage content (plot 706) of the SCR catalyst. Herein, since the ammonia content is relatively higher at the time of shift from VDE to non-VDE mode, a rich fuel injection of a lower rich bias and of a shorter duration d1 is used to regenerate the TWC. That is, a relatively lower fuel penalty is incurred. While the TWC is being regenerated, the ammonia stored on the SCR catalyst may be consumed to reduce exhaust NOx species, such that an exhaust NOx level at the time of shift from VDE mode to non-VDE mode is substantially maintained (plot 712, solid line).

An alternate regeneration is shown at plots 704, 707, 710, 713 (dashed lines) wherein an exhaust combustion ratio is not adjusted during the VDE mode (for engine exhaust configuration of FIG. 2B) or prior to the VDE mode (for engine exhaust configuration of FIG. 2A or in-line engines) to pre-charge the SCR catalyst. Herein, during the VDE mode, the combustion AFR is maintained at stoichiometry 705 during the VDE mode (plot 704). The ammonia content (plot 707) of the SCR catalyst drops during the VDE mode as the ammonia is used to reduce exhaust NOx at the SCR catalyst rather than at the TWC. Consequently, at t2, when the engine is shifted to the non-VDE mode, in addition to reactivating engine cylinders, a controller may regenerate the TWC by enriching the combustion air-to-fuel ratio (plot 704) for a second, longer duration d2 and/or of a higher rich bias to bring the regeneration state of the TWC (plot 710) above threshold state 711. The degree of richness of the rich fuel injection is adjusted based on the ammonia storage content (plot 707) of the SCR catalyst. Herein, since the ammonia content is relatively lower at the time of shift from VDE to non-VDE mode, a rich fuel injection of a higher rich bias and of a longer duration d2 is used to regenerate the TWC. That is, a relatively higher fuel penalty is incurred. In addition, while the TWC is being regenerated, the lower ammonia content of the SCR catalyst causes a NOx spike at the time of shift from VDE mode to non-VDE mode is substantially maintained (plot 713).

It will be appreciated that while the lower ammonia content of the SCR catalyst leads to a higher fuel penalty, this penalty may be still lower than a fuel penalty that would be incurred if no upstream exhaust catalyst were included in the emission control device. In particular, in the absence of the SCR catalyst, ammonia generated during stoichiometric engine operation would be stored on the three-way catalyst. Subsequent oxidation of the ammonia to NOx due to fresh air from the inactive cylinders would not only lead to a higher NOx spike but would also lead to oxidation of the TWC, which would then require a much larger fuel penalty to regenerate.

It will be appreciated that while the example of FIG. 7 is explained with reference to a VDE event as the lean engine event, in an alternate example, the lean event may be an engine idle-stop. Therein, the same trends would be seen during a restart from the engine isle-stop as depicted here during the shift from VDE to non-VDE mode.

In this way, an air-to-fuel ratio may be adjusted during or prior to an engine lean event (such as during/prior to cylinders being deactivated, a DFSO operation, or an engine idle-stop) to charge an upstream underbody exhaust SCR catalyst with ammonia and protect a downstream underbody three-way catalyst from being charged with the ammonia. By using the stored ammonia during a subsequent shift out of the lean event (such as when restarting from idle-stop or reactivating engine cylinders), an amount of fuel required to regenerate the close coupled three-way catalyst as well as the underbody three-way catalyst can be reduced, providing fuel economy benefits. In addition, by using the stored ammonia to reduce exhaust NOx at the SCR catalyst while the three-way catalyst is regenerated, NOx spikes during the shift can be reduced and exhaust emissions can be controlled. This allows fuel economy benefits from engine idle-stop operations and/or VDE operations to be achieved without degrading exhaust emissions.

Note that the example control and estimation routines included herein can be used with various engine and/or vehicle system configurations. The specific routines described herein may represent one or more of any number of processing strategies such as event-driven, interrupt-driven, multi-tasking, multi-threading, and the like. As such, various acts, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated acts or functions may be repeatedly performed depending on the particular strategy being used. Further, the described acts may graphically represent code to be programmed into the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein. The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An engine method, comprising:
   during engine running, flowing exhaust through each of a first, second, and third catalyst to store at least some exhaust ammonia on the first catalyst, the second catalyst located downstream of, and the third catalyst located upstream of, the first catalyst;
   selectively deactivating the engine during an idle-stop; and
   during an engine restart from idle-stop, adjusting regeneration of the third catalyst based on an ammonia content of the first catalyst.

2. The method of claim 1, wherein the first catalyst is an SCR catalyst and the second and third catalysts are three-way catalysts, the method further comprising, after regenerating the third catalyst, in response to a high load engine operation, adjusting regeneration of the second catalyst.

3. The method of claim 2, wherein regenerating the third catalyst includes, during the engine restart, adjusting a fuel injection to the engine to provide an exhaust air-to-fuel ratio that is richer than stoichiometry to regenerate the third catalyst.

4. The method of claim 3, wherein adjusting the regeneration includes, as the ammonia content of the first catalyst increases above a threshold, reducing a degree of richness of the regenerating fuel injection.

5. The method of claim 3, wherein the adjusting further includes, as the ammonia content of the first catalyst increases above a threshold, reducing a duration of regenerating the third catalyst with the rich fuel injection.

6. The method of claim 3, wherein adjusting the regeneration includes, as the ammonia content of the first catalyst decreases below a threshold, increasing a degree of richness of the regenerating fuel injection.

7. The method of claim 1, wherein the first catalyst and the second catalyst are integrated with face-sharing contact in an emission control device coupled to an engine exhaust manifold.

8. The method of claim 1, wherein an ammonia content of the first catalyst is based at least on a duration of the immediately preceding idle-stop.

9. The method of claim 1, wherein the engine is coupled to a vehicle, and wherein an ammonia content of the first catalyst is based at least on a number of engine idle-stop events estimated over a duration of vehicle operation.

10. An engine method comprising:
    during a first engine restart from idle-stop, when an ammonia content of a first exhaust catalyst is higher than a threshold, injecting fuel with a first, lower rich bias to regenerate each of a second and third, exhaust catalyst, the second exhaust catalyst positioned downstream of the first catalyst, the third exhaust catalyst positioned upstream of the first catalyst; and
    during a second engine restart from idle-stop, when an ammonia content of the first exhaust catalyst is lower than the threshold, injecting fuel with a second, higher rich bias to regenerate the second and third exhaust catalysts.

11. The method of claim 10, wherein during each of the first and second engine restarts, the ammonia content of the first catalyst is based at least on a duration of an immediately preceding idle-stop.

12. The method of claim 11, wherein during each of the first and second engine restarts, the ammonia content of the first catalyst is further based on one or more engine operating conditions estimated during engine running prior to the idle-stop, the one or more conditions including exhaust gas temperature, exhaust flow rate, engine speed, engine load, and exhaust air-to-fuel ratio.

13. The method of claim 10, wherein during each of the first and second engine restarts, exhaust gas is flowed through the third catalyst followed by the first catalyst and then the second catalyst before venting to atmosphere.

14. The method of claim 10, wherein the first catalyst and the second catalyst are integrated in an emission control device coupled to an exhaust manifold of the engine.

15. An engine system, comprising:
    an engine that is selectively deactivatable responsive to idle-stop conditions;
    an emission control device coupled to an engine exhaust manifold, the device including a first, upstream catalyst in face-sharing contact with a second, downstream catalyst;
    a third exhaust catalyst positioned upstream of the emission control device; and
    a control system with computer readable instructions for,
    during an engine restart from idle-stop, adjusting fuel injection to be richer than stoichiometry to regenerate the third catalyst, a degree of richness adjusted based on an ammonia content of the first catalyst.

16. The system of claim 15, wherein the ammonia content of the first catalyst at the engine restart is based on the idle-stop, the ammonia content of the first catalyst at engine restart decreased as a duration of the idle-stop increases.

17. The system of claim 16, wherein the adjusting includes, as the ammonia content of the first catalyst decreases, increasing a degree of richness of the fuel injection.

18. The system of claim 16, wherein the ammonia content of the first catalyst at engine restart is further based on a temperature of the emission control device.

19. The system of claim 15, wherein the first catalyst has a higher ammonia storage content than the second catalyst.

20. The system of claim 15, wherein the controller includes further instructions for,
    prior to the idle-stop, adjusting fuel injection to the engine to be richer than stoichiometry, a degree of richness adjusted responsive to an ammonia content of the first catalyst to maintain the ammonia content of the first catalyst above a threshold amount.

* * * * *